(12) United States Patent
Doherty et al.

(10) Patent No.: US 8,034,587 B2
(45) Date of Patent: Oct. 11, 2011

(54) PROKARYOTIC DNA REPAIR LIGASES

(75) Inventors: Aidan Doherty, Cambridge (GB); Marina Della, Cambridge (GB); Geoffrey Weller, Cambridge (GB); Stephen Jackson, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 746 days.

(21) Appl. No.: 10/568,055

(22) PCT Filed: Aug. 2, 2004

(86) PCT No.: PCT/GB2004/003349
§ 371 (c)(1),
(2), (4) Date: Sep. 27, 2006

(87) PCT Pub. No.: WO2005/017140
PCT Pub. Date: Feb. 24, 2005

(65) Prior Publication Data
US 2007/0172822 A1 Jul. 26, 2007

Related U.S. Application Data

(60) Provisional application No. 60/494,088, filed on Aug. 12, 2003.

(51) Int. Cl.
*C12P 19/34* (2006.01)
*C12N 9/12* (2006.01)

(52) U.S. Cl. ...... 435/91.1; 435/183; 435/194; 435/91.4; 435/91.51; 435/91.52

(58) Field of Classification Search ...................... None
See application file for complete search history.

(56) References Cited

U.S. PATENT DOCUMENTS 5,976,806 A * 11/1999 Mahajan et al. .................. 435/6

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Srivastava et al., Journal of Biological Chemistry, vol. 280, No. 34, pp. 30273-30281, 2005.*
Cole et al., Uniprot Accession No. P71571, May 30, 2000.*
Aravind et al., "Prokaryotic homologs of the eukaryotic DNA-end-binding protein Ku, novel domains in the Ku protein and prediction of a porkayrotic double-strand break repair system," 11:1365-1374 (2001), Genome Research.
Doherty et al., "Identification of bacterial homologues of the Ku DNA repair proteins," FEBS Letters, 500:186-188 (2001).
Weller et al., "A family of DNA repair ligares in bacteria?" FEBS Letters, 505:340-342, 2001.
Weller et al., "Identification of a DNA nonhomologous end-jointing complex in bacteria," *Science*, 297:1686-1689 (2002).

* cited by examiner

*Primary Examiner* — Richard Hutson
(74) *Attorney, Agent, or Firm* — Klarquist Sparkman, LLP

(57) ABSTRACT

The present invention relates to the cloning and characterization of a prokaryotic DNA repair ligase, which is shown to possess a range of activities that allow the ligation and repair of non-compatible DNA ends and double strand breaks (DSBs). The enzyme has a range of applications in the manipulation and cloning of nucleic acids.

12 Claims, 13 Drawing Sheets

A.

B.

C.

A

B

C

HO(+2)   TACTGT̲   GCG
         ATG   A̲CAACGC

HO(-1)   TACTGT̲GCG
         ATG  A̲CGC

Figure 12

SEQUENCE LISTING

<160> NUMBER OF SEQ ID NOS: 92

<210> SEQ ID NO 1
<211> LENGTH: 10
<212> TYPE: PRT
<213> ORGANISM: Artificial sequence
<220> FEATURE:
<223> OTHER INFORMATION: Conserved motif

<400> SEQUENCE: 1

Arg Leu Val Phe Asp Leu Asp Pro Gly Glu
1               5                   10

<210> SEQ ID NO 2
<211> LENGTH: 10
<212> TYPE: PRT
<213> ORGANISM: Artificial sequence
<220> FEATURE:
<223> OTHER INFORMATION: Conserved motif

<400> SEQUENCE: 2

Ser Gly Ser Lys Gly Leu His Leu Tyr Thr
1               5                   10

<210> SEQ ID NO 3
<211> LENGTH: 6
<212> TYPE: PRT
<213> ORGANISM: Artificial sequence
<220> FEATURE:
<223> OTHER INFORMATION: Conserved motif

<400> SEQUENCE: 3

Lys Val Phe Val Asp Trp
1               5

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
atgcgagcca tttggacggg                                                    20

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
ggatcctcac ggaggcgttg ggacg                                              25

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
atgggttcgg cgtcggagca                                                    20

```
<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
tcctcattcg cgcaccacct cactgg                                              26

<210> SEQ ID NO 8
<211> LENGTH: 15
<212> TYPE: DNA
<213> ORGANISM: Artificial sequence
<220> FEATURE:
<223> OTHER INFORMATION: Oligonucleotide

<400> SEQUENCE: 8
ctgcagctga tgcgc                                                          15

<210> SEQ ID NO 9
<211> LENGTH: 20
<212> TYPE: DNA
<213> ORGANISM: Artificial sequence
<220> FEATURE:
<223> OTHER INFORMATION: Oligonucleotide

<400> SEQUENCE: 9
atccggcgca tcagctgcag                                                     20

<210> SEQ ID NO 10
<211> LENGTH: 25
<212> TYPE: DNA
<213> ORGANISM: Artificial sequence
<220> FEATURE:
<223> OTHER INFORMATION: Oligonucleotide

<400> SEQUENCE: 10
agtcgatcct gcgcatcatc tgcag                                               25

<210> SEQ ID NO 11
<211> LENGTH: 41
<212> TYPE: DNA
<213> ORGANISM: Artificial sequence
<220> FEATURE:
<223> OTHER INFORMATION: Oligonucleotide

<400> SEQUENCE: 11
acccggggat ccgtacagtc tatccggcgc atcagctgca g                             41

<210> SEQ ID NO 12
<211> LENGTH: 50
<212> TYPE: DNA
<213> ORGANISM: Artificial sequence
<220> FEATURE:
<223> OTHER INFORMATION: 50mer substrate

<400> SEQUENCE: 12
gtaacaaagt ttggattgct actgaccgct ctcgtgctcg tcgctgcgtt                    50

<210> SEQ ID NO 13
<211> LENGTH: 50
<212> TYPE: DNA
<213> ORGANISM: Artificial sequence
<220> FEATURE:
<223> OTHER INFORMATION: Oligonucleotide

<400> SEQUENCE: 13
```
gtctgtctca ctattagaac cctttagagt catgcgtcgc gaggcaacgc        50

<210> SEQ ID NO 14
<211> LENGTH: 43
<212> TYPE: DNA
<213> ORGANISM: Artificial sequence
<220> FEATURE:
<223> OTHER INFORMATION: Oligonucleotide

<400> SEQUENCE: 14
gcctcgcgac gcatgactct aaagggttct aatagtgaga cag               43

<210> SEQ ID NO 15
<211> LENGTH: 41
<212> TYPE: DNA
<213> ORGANISM: Artificial sequence
<220> FEATURE:
<223> OTHER INFORMATION: Oligonucleotide

<400> SEQUENCE: 15
gcgacgagca cgagagcggt cagtagcaat ccaaactttg t                 41

<210> SEQ ID NO 16
<211> LENGTH: 50
<212> TYPE: DNA
<213> ORGANISM: Artificial sequence
<220> FEATURE:
<223> OTHER INFORMATION: Oligonucleotide

<400> SEQUENCE: 16
gtaacaaagt ttggattgct actgaccgct ctcgtgctcg tcgctgcgtt        50

<210> SEQ ID NO 17
<211> LENGTH: 52
<212> TYPE: DNA
<213> ORGANISM: Artificial sequence
<220> FEATURE:
<223> OTHER INFORMATION: Oligonucleotide

<400> SEQUENCE: 17
ctgtctgtct cactattaga accctttaga gtcatgcgtc gcgaggcaac gc     52

<210> SEQ ID NO 18
<211> LENGTH: 20
<212> TYPE: DNA
<213> ORGANISM: Artificial sequence
<220> FEATURE:
<223> OTHER INFORMATION: Oligonucleotide

<400> SEQUENCE: 18
gaaaccacgt accggcgtgt                                         20

<210> SEQ ID NO 19
<211> LENGTH: 13
<212> TYPE: DNA
<213> ORGANISM: Artificial sequence
<220> FEATURE:
<223> OTHER INFORMATION: Oligonucleotide

<400> SEQUENCE: 19
ctttggtcga tgg                                                13

<210> SEQ ID NO 20
<211> LENGTH: 26
<212> TYPE: DNA
<213> ORGANISM: Artificial sequence

```
<220> FEATURE:
<223> OTHER INFORMATION: Oligonucleotide

<400> SEQUENCE: 20
ctgcagatca tgcgccggat tgcccc                                        26

<210> SEQ ID NO 21
<211> LENGTH: 17
<212> TYPE: DNA
<213> ORGANISM: Artificial sequence
<220> FEATURE:
<223> OTHER INFORMATION: Oligonucleotide

<400> SEQUENCE: 21
gacgtctagt acgcggc                                                  17

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
caagtatgga tctcgaggtt                                               20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
ctgttctaga ggtacctagt                                               20

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
ccttaagttg aacggagtcc                                               20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
cttgactagc gcactaccag                                               20

<210> SEQ ID NO 26
<211> LENGTH: 21
<212> TYPE: DNA
<213> ORGANISM: Artificial sequence
<220> FEATURE:
<223> OTHER INFORMATION: Primer

<400> SEQUENCE: 26
ggcaggagaa ttttcagcat c                                             21
```

```
<210> SEQ ID NO 27
<211> LENGTH: 8
<212> TYPE: PRT
<213> ORGANISM: Bacillus subtilis

<400> SEQUENCE: 27

Glu Val Lys Tyr Asp Gly Tyr Arg
1               5

<210> SEQ ID NO 28
<211> LENGTH: 8
<212> TYPE: PRT
<213> ORGANISM: Bacillus subtilis

<400> SEQUENCE: 28

Leu Thr Leu Asp Gly Glu Ile Val
1               5

<210> SEQ ID NO 29
<211> LENGTH: 12
<212> TYPE: PRT
<213> ORGANISM: Bacillus subtilis

<400> SEQUENCE: 29

Cys Phe Leu Ala Phe Asp Leu Leu Glu Arg Ser Gly
1               5                   10

<210> SEQ ID NO 30
<211> LENGTH: 5
<212> TYPE: PRT
<213> ORGANISM: Bacillus subtilis

<400> SEQUENCE: 30

Glu Gly Ile Val Ala
1               5

<210> SEQ ID NO 31
<211> LENGTH: 11
<212> TYPE: PRT
<213> ORGANISM: Bacillus subtilis

<400> SEQUENCE: 31

Trp Leu Lys Tyr Lys Asn Phe Lys Gln Ala Tyr
1               5                   10

<210> SEQ ID NO 32
<211> LENGTH: 11
<212> TYPE: PRT
<213> ORGANISM: Bacillus subtilis

<400> SEQUENCE: 32

Ile Gly Phe Glu Phe Gln Met Asp Trp Thr Glu
1               5                   10

<210> SEQ ID NO 33
<211> LENGTH: 8
<212> TYPE: PRT
<213> ORGANISM: Bacillus halodurans

<400> SEQUENCE: 33

Glu Val Lys Tyr Asp Gly Phe Arg
1               5

<210> SEQ ID NO 34
<211> LENGTH: 8
<212> TYPE: PRT
```

```
<213> ORGANISM: Bacillus halodurans

<400> SEQUENCE: 34

Ile Thr Ile Asp Gly Glu Leu Val
1               5

<210> SEQ ID NO 35
<211> LENGTH: 12
<212> TYPE: PRT
<213> ORGANISM: Bacillus halodurans

<400> SEQUENCE: 35

Thr Leu Leu Ala Phe Asp Ile Leu Glu Leu Lys Gly
1               5                   10

<210> SEQ ID NO 36
<211> LENGTH: 5
<212> TYPE: PRT
<213> ORGANISM: Bacillus halodurans

<400> SEQUENCE: 36

Glu Gly Val Val Ala
1               5

<210> SEQ ID NO 37
<211> LENGTH: 11
<212> TYPE: PRT
<213> ORGANISM: Bacillus halodurans

<400> SEQUENCE: 37

Trp Leu Lys Lys Lys Asn Phe Arg Gln Val Thr
1               5                   10

<210> SEQ ID NO 38
<211> LENGTH: 11
<212> TYPE: PRT
<213> ORGANISM: Bacillus halodurans

<400> SEQUENCE: 38

His Arg Phe Arg Leu Asp Val Lys Pro Ala Gln
1               5                   10

<210> SEQ ID NO 39
<211> LENGTH: 8
<212> TYPE: PRT
<213> ORGANISM: Mycobacterium tuberculosis

<400> SEQUENCE: 39

Glu Pro Lys Trp Asp Gly Phe Arg
1               5

<210> SEQ ID NO 40
<211> LENGTH: 8
<212> TYPE: PRT
<213> ORGANISM: Mycobacterium tuberculosis

<400> SEQUENCE: 40

Cys Val Ile Asp Gly Glu Ile Ile
1               5

<210> SEQ ID NO 41
<211> LENGTH: 12
<212> TYPE: PRT
<213> ORGANISM: Mycobacterium tuberculosis

<400> SEQUENCE: 41
```

```
Ser Phe Ile Ala Phe Asp Leu Leu Ala Leu Gly Asp
1               5                   10

<210> SEQ ID NO 42
<211> LENGTH: 5
<212> TYPE: PRT
<213> ORGANISM: Mycobacterium tuberculosis

<400> SEQUENCE: 42

Asp Gly Val Ile Ala
1               5

<210> SEQ ID NO 43
<211> LENGTH: 11
<212> TYPE: PRT
<213> ORGANISM: Mycobacterium tuberculosis

<400> SEQUENCE: 43

Met Phe Lys Ile Lys His Leu Arg Thr Ala Asp
1               5                   10

<210> SEQ ID NO 44
<211> LENGTH: 11
<212> TYPE: PRT
<213> ORGANISM: Mycobacterium tuberculosis

<400> SEQUENCE: 44

Thr Ala Gln Phe Asn Arg Trp Arg Pro Asp Arg
1               5                   10

<210> SEQ ID NO 45
<211> LENGTH: 8
<212> TYPE: PRT
<213> ORGANISM: Bacillus subtilis

<400> SEQUENCE: 45

Glu Leu Lys Phe Asp Gly Ile Arg
1               5

<210> SEQ ID NO 46
<211> LENGTH: 8
<212> TYPE: PRT
<213> ORGANISM: Bacillus subtilis

<400> SEQUENCE: 46

Thr Val Leu Asp Gly Glu Val Ile
1               5

<210> SEQ ID NO 47
<211> LENGTH: 12
<212> TYPE: PRT
<213> ORGANISM: Bacillus subtilis

<400> SEQUENCE: 47

Val Tyr Cys Val Phe Asp Val Ile Tyr Lys Asp Gly
1               5                   10

<210> SEQ ID NO 48
<211> LENGTH: 5
<212> TYPE: PRT
<213> ORGANISM: Bacillus subtilis

<400> SEQUENCE: 48

Glu Gly Ile Val Ile
1               5
```

```
<210> SEQ ID NO 49
<211> LENGTH: 11
<212> TYPE: PRT
<213> ORGANISM: Bacillus subtilis

<400> SEQUENCE: 49

Trp Leu Lys Val Ile Asn Tyr Asp Tyr Thr Glu
1               5                   10

<210> SEQ ID NO 50
<211> LENGTH: 8
<212> TYPE: PRT
<213> ORGANISM: Pseudomonas aeruginosa

<400> SEQUENCE: 50

Glu Leu Lys Leu Asp Gly Tyr Arg
1               5

<210> SEQ ID NO 51
<211> LENGTH: 8
<212> TYPE: PRT
<213> ORGANISM: Pseudomonas aeruginosa

<400> SEQUENCE: 51

Ser Trp Leu Asp Gly Glu Leu Val
1               5

<210> SEQ ID NO 52
<211> LENGTH: 12
<212> TYPE: PRT
<213> ORGANISM: Pseudomonas aeruginosa

<400> SEQUENCE: 52

Leu Tyr Val Leu Phe Asp Leu Pro Tyr His Glu Gly
1               5                   10

<210> SEQ ID NO 53
<211> LENGTH: 5
<212> TYPE: PRT
<213> ORGANISM: Pseudomonas aeruginosa

<400> SEQUENCE: 53

Glu Gly Val Ile Gly
1               5

<210> SEQ ID NO 54
<211> LENGTH: 11
<212> TYPE: PRT
<213> ORGANISM: Pseudomonas aeruginosa

<400> SEQUENCE: 54

Trp Ile Lys Leu Lys Cys Gln Leu Arg Gln Glu
1               5                   10

<210> SEQ ID NO 55
<211> LENGTH: 11
<212> TYPE: PRT
<213> ORGANISM: Pseudomonas aeruginosa

<400> SEQUENCE: 55

Ala Arg Glu Val Thr Gly Glu Arg Pro Ala Gly
1               5                   10

<210> SEQ ID NO 56
```

```
<211> LENGTH: 8
<212> TYPE: PRT
<213> ORGANISM: Mycobacterium tuberculosis

<400> SEQUENCE: 56

Glu Gly Lys Trp Asp Gly Tyr Arg
1               5

<210> SEQ ID NO 57
<211> LENGTH: 8
<212> TYPE: PRT
<213> ORGANISM: Mycobacterium tuberculosis

<400> SEQUENCE: 57

Val Val Leu Asp Gly Glu Ala Val
1               5

<210> SEQ ID NO 58
<211> LENGTH: 12
<212> TYPE: PRT
<213> ORGANISM: Mycobacterium tuberculosis

<400> SEQUENCE: 58

Glu Phe Trp Ala Phe Asp Leu Leu Tyr Leu Asp Gly
1               5                   10

<210> SEQ ID NO 59
<211> LENGTH: 5
<212> TYPE: PRT
<213> ORGANISM: Mycobacterium tuberculosis

<400> SEQUENCE: 59

Glu Gly Val Ile Ala
1               5

<210> SEQ ID NO 60
<211> LENGTH: 11
<212> TYPE: PRT
<213> ORGANISM: Mycobacterium tuberculosis

<400> SEQUENCE: 60

Trp Val Lys Asp Lys His Trp Asn Thr Gln Glu
1               5                   10

<210> SEQ ID NO 61
<211> LENGTH: 10
<212> TYPE: PRT
<213> ORGANISM: Mycobacterium tuberculosis

<400> SEQUENCE: 61

Ser Ser Trp Arg Gly Leu Arg Pro Asp Lys
1               5                   10

<210> SEQ ID NO 62
<211> LENGTH: 6
<212> TYPE: PRT
<213> ORGANISM: Artificial sequence
<220> FEATURE:
<223> OTHER INFORMATION: Bact ATP Consensus
<220> FEATURE:
<221> NAME/KEY: MISC_FEATURE
<222> LOCATION: (2)..(2)
<223> OTHER INFORMATION: Xaa is hydrophobic
<220> FEATURE:
<221> NAME/KEY: MISC_FEATURE
<222> LOCATION: (5)..(5)
<223> OTHER INFORMATION: Xaa is hydrophobic
```

```
<400> SEQUENCE: 62

Lys Xaa Asp Gly Xaa Arg
1               5

<210> SEQ ID NO 63
<211> LENGTH: 6
<212> TYPE: PRT
<213> ORGANISM: Artificial sequence
<220> FEATURE:
<223> OTHER INFORMATION: Bact ATP Consensus
<220> FEATURE:
<221> NAME/KEY: MISC_FEATURE
<222> LOCATION: (1)..(1)
<223> OTHER INFORMATION: Xaa is hydrophobic
<220> FEATURE:
<221> NAME/KEY: MISC_FEATURE
<222> LOCATION: (5)..(6)
<223> OTHER INFORMATION: Xaa is hydrophobic
<220> FEATURE:
<221> NAME/KEY: MISC_FEATURE
<222> LOCATION: (2)..(2)
<223> OTHER INFORMATION: Xaa is polar

<400> SEQUENCE: 63

Xaa Xaa Gly Glu Xaa Xaa
1               5

<210> SEQ ID NO 64
<211> LENGTH: 4
<212> TYPE: PRT
<213> ORGANISM: Artificial sequence
<220> FEATURE:
<223> OTHER INFORMATION: Bact ATP Consensus
<220> FEATURE:
<221> NAME/KEY: MISC_FEATURE
<222> LOCATION: (1)..(1)
<223> OTHER INFORMATION: Xaa is hydrophobic
<220> FEATURE:
<221> NAME/KEY: MISC_FEATURE
<222> LOCATION: (4)..(4)
<223> OTHER INFORMATION: Xaa is hydrophobic

<400> SEQUENCE: 64

Xaa Phe Asp Xaa
1

<210> SEQ ID NO 65
<211> LENGTH: 5
<212> TYPE: PRT
<213> ORGANISM: Artificial sequence
<220> FEATURE:
<223> OTHER INFORMATION: Bact ATP Consensus
<220> FEATURE:
<221> NAME/KEY: MISC_FEATURE
<222> LOCATION: (3)..(5)
<223> OTHER INFORMATION: Xaa is hydrophobic

<400> SEQUENCE: 65

Glu Gly Xaa Xaa Xaa
1               5

<210> SEQ ID NO 66
<211> LENGTH: 8
<212> TYPE: PRT
<213> ORGANISM: T7

<400> SEQUENCE: 66

Glu Ile Lys Tyr Asp Gly Val Arg
1               5
```

-continued

```
<210> SEQ ID NO 67
<211> LENGTH: 8
<212> TYPE: PRT
<213> ORGANISM: T7

<400> SEQUENCE: 67

Phe Met Leu Asp Gly Glu Leu Met
1               5

<210> SEQ ID NO 68
<211> LENGTH: 10
<212> TYPE: PRT
<213> ORGANISM: T7

<400> SEQUENCE: 68

His Ile Lys Leu Tyr Ala Ile Leu Pro Leu
1               5                   10

<210> SEQ ID NO 69
<211> LENGTH: 5
<212> TYPE: PRT
<213> ORGANISM: T7

<400> SEQUENCE: 69

Glu Gly Leu Ile Val
1               5

<210> SEQ ID NO 70
<211> LENGTH: 11
<212> TYPE: PRT
<213> ORGANISM: T7

<400> SEQUENCE: 70

Trp Trp Lys Met Lys Pro Glu Asn Glu Ala Asp
1               5                   10

<210> SEQ ID NO 71
<211> LENGTH: 10
<212> TYPE: PRT
<213> ORGANISM: T7

<400> SEQUENCE: 71

Pro Ser Phe Val Met Phe Arg Gly Thr Glu
1               5                   10

<210> SEQ ID NO 72
<211> LENGTH: 10
<212> TYPE: PRT
<213> ORGANISM: Mycobacterium tuberculosis

<400> SEQUENCE: 72

Arg Leu Val Phe Asp Leu Asp Pro Gly Glu
1               5                   10

<210> SEQ ID NO 73
<211> LENGTH: 10
<212> TYPE: PRT
<213> ORGANISM: Mycobacterium tuberculosis

<400> SEQUENCE: 73

Ser Gly Ser Lys Gly Leu His Leu Tyr Thr
1               5                   10

<210> SEQ ID NO 74
<211> LENGTH: 6
<212> TYPE: PRT
```

```
<213> ORGANISM: Mycobacterium tuberculosis

<400> SEQUENCE: 74

Lys Val Phe Val Asp Trp
1               5

<210> SEQ ID NO 75
<211> LENGTH: 10
<212> TYPE: PRT
<213> ORGANISM: Homo sapiens

<400> SEQUENCE: 75

Glu Leu Val Phe Asp Ile Asp Met Thr Asp
1               5                   10

<210> SEQ ID NO 76
<211> LENGTH: 10
<212> TYPE: PRT
<213> ORGANISM: Homo sapiens

<400> SEQUENCE: 76

Ser Gly Arg Arg Gly Val His Cys Trp Val
1               5                   10

<210> SEQ ID NO 77
<211> LENGTH: 6
<212> TYPE: PRT
<213> ORGANISM: Homo sapiens

<400> SEQUENCE: 77

Phe Pro Arg Leu Asp Ile
1               5

<210> SEQ ID NO 78
<211> LENGTH: 6
<212> TYPE: PRT
<213> ORGANISM: Mus musculus

<400> SEQUENCE: 78

Phe Pro Arg Leu Asp Val
1               5

<210> SEQ ID NO 79
<211> LENGTH: 10
<212> TYPE: PRT
<213> ORGANISM: Drosophila melanogaster

<400> SEQUENCE: 79

Ser Gly Arg Arg Gly Ile His Cys Trp Val
1               5                   10

<210> SEQ ID NO 80
<211> LENGTH: 6
<212> TYPE: PRT
<213> ORGANISM: Drosophila melanogaster

<400> SEQUENCE: 80

Tyr Pro Arg Leu Asp Ile
1               5

<210> SEQ ID NO 81
<211> LENGTH: 10
<212> TYPE: PRT
<213> ORGANISM: Saccharomyces cerevisiae

<400> SEQUENCE: 81
```

-continued

Glu Leu Val Phe Asp Ile Asp Met Asp Asp
1               5                   10

<210> SEQ ID NO 82
<211> LENGTH: 10
<212> TYPE: PRT
<213> ORGANISM: Saccharomyces cerevisiae

<400> SEQUENCE: 82

Ser Gly Arg Arg Gly Ala His Cys Trp Val
1               5                   10

<210> SEQ ID NO 83
<211> LENGTH: 6
<212> TYPE: PRT
<213> ORGANISM: Saccharomyces cerevisiae

<400> SEQUENCE: 83

Tyr Pro Lys Leu Asp Val
1               5

<210> SEQ ID NO 84
<211> LENGTH: 10
<212> TYPE: PRT
<213> ORGANISM: Schizosaccharomyces pombe

<400> SEQUENCE: 84

Ser Gly Arg Arg Gly Ile His Ala Trp Ile
1               5                   10

<210> SEQ ID NO 85
<211> LENGTH: 6
<212> TYPE: PRT
<213> ORGANISM: Schizosaccharomyces pombe

<400> SEQUENCE: 85

Tyr Pro Arg Leu Asp Val
1               5

<210> SEQ ID NO 86
<211> LENGTH: 13
<212> TYPE: DNA
<213> ORGANISM: Artificial sequence
<220> FEATURE:
<223> OTHER INFORMATION: Synthetic oligomer

<400> SEQUENCE: 86
ggtacgtggt ttc                                                        13

<210> SEQ ID NO 87
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 87
cggcgcatga tctgcag                                                    17

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 88
gaaaccacgt accggggtgt                                                    20

<210> SEQ ID NO 89
<211> LENGTH: 39
<212> TYPE: DNA
<213> ORGANISM: Artificial sequence
<220> FEATURE:
<223> OTHER INFORMATION: Synthetic oligomer

<400> SEQUENCE: 89
ctgcagatca tgcgccggat tgccccggta cgtggtttc                               39

<210> SEQ ID NO 90
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 90
gaaaccacgt accggggcaa tccggcgcat gatctgcag                               39

<210> SEQ ID NO 91
<211> LENGTH: 759
<212> TYPE: PRT
<213> ORGANISM: Mycobacterium tuberculosis

<400> SEQUENCE: 91

Met Gly Ser Ala Ser Glu Gln Arg Val Thr Leu Thr Asn Ala Asp Lys
1               5                   10                  15

Val Leu Tyr Pro Ala Thr Gly Thr Thr Lys Ser Asp Ile Phe Asp Tyr
            20                  25                  30

Tyr Ala Gly Val Ala Glu Val Met Leu Gly His Ile Ala Gly Arg Pro
        35                  40                  45

Ala Thr Arg Lys Arg Trp Pro Asn Gly Val Asp Gln Pro Ala Phe Phe
    50                  55                  60

Glu Lys Gln Leu Ala Leu Ser Ala Pro Pro Trp Leu Ser Arg Ala Thr
65                  70                  75                  80

Val Ala His Arg Ser Gly Thr Thr Thr Tyr Pro Ile Ile Asp Ser Ala
                85                  90                  95

Thr Gly Leu Ala Trp Ile Ala Gln Gln Ala Ala Leu Glu Val His Val
            100                 105                 110

Pro Gln Trp Arg Phe Val Ala Glu Pro Gly Ser Gly Leu Asn Pro
        115                 120                 125

Gly Pro Ala Thr Arg Leu Val Phe Asp Leu Asp Pro Gly Glu Gly Val
    130                 135                 140

Met Met Ala Gln Leu Ala Glu Val Ala Arg Ala Val Arg Asp Leu Leu
145                 150                 155                 160

Ala Asp Ile Gly Leu Val Thr Phe Pro Val Thr Ser Gly Ser Lys Gly
                165                 170                 175

Leu His Leu Tyr Thr Pro Leu Asp Glu Pro Val Ser Ser Arg Gly Ala
            180                 185                 190

Thr Val Leu Ala Lys Arg Val Ala Gln Arg Leu Glu Gln Ala Met Pro
        195                 200                 205

Ala Leu Val Thr Ser Thr Met Thr Lys Ser Leu Arg Ala Gly Lys Val
    210                 215                 220

Phe Val Asp Trp Ser Gln Asn Ser Gly Ser Lys Thr Thr Ile Ala Pro
225                 230                 235                 240
```

```
Tyr Ser Leu Arg Gly Arg Thr His Pro Thr Val Ala Ala Pro Arg Thr
                245                 250                 255

Trp Ala Glu Leu Asp Asp Pro Ala Leu Arg Gln Leu Ser Tyr Asp Glu
        260                 265                 270

Val Leu Thr Arg Ile Ala Arg Asp Gly Asp Leu Leu Glu Arg Leu Asp
            275                 280                 285

Ala Asp Ala Pro Val Ala Asp Arg Leu Thr Arg Tyr Arg Arg Met Arg
290                 295                 300

Asp Ala Ser Lys Thr Pro Glu Pro Ile Pro Thr Ala Lys Pro Val Thr
305                 310                 315                 320

Gly Asp Gly Asn Thr Phe Val Ile Gln Glu His Ala Arg Arg Pro
                325                 330                 335

His Tyr Asp Phe Arg Leu Glu Cys Asp Gly Val Leu Val Ser Trp Ala
            340                 345                 350

Val Pro Lys Asn Leu Pro Asp Asn Thr Ser Val Asn His Leu Ala Ile
        355                 360                 365

His Thr Glu Asp His Pro Leu Glu Tyr Ala Thr Phe Glu Gly Ala Ile
    370                 375                 380

Pro Ser Gly Glu Tyr Gly Ala Gly Lys Val Ile Ile Trp Asp Ser Gly
385                 390                 395                 400

Thr Tyr Asp Thr Glu Lys Phe His Asp Asp Pro His Thr Gly Glu Val
                405                 410                 415

Ile Val Asn Leu His Gly Gly Arg Ile Ser Gly Arg Tyr Ala Leu Ile
            420                 425                 430

Arg Thr Asn Gly Asp Arg Trp Leu Ala His Arg Leu Lys Asn Gln Lys
        435                 440                 445

Asp Gln Lys Val Phe Glu Phe Asp Asn Leu Ala Pro Met Leu Ala Thr
    450                 455                 460

His Gly Thr Val Ala Gly Leu Lys Ala Ser Gln Trp Ala Phe Glu Gly
465                 470                 475                 480

Lys Trp Asp Gly Tyr Arg Leu Leu Val Glu Ala Asp His Gly Ala Val
                485                 490                 495

Arg Leu Arg Ser Arg Ser Gly Arg Asp Val Thr Ala Glu Tyr Pro Gln
            500                 505                 510

Leu Arg Ala Leu Ala Glu Asp Leu Ala Asp His Val Val Leu Asp
        515                 520                 525

Gly Glu Ala Val Val Leu Asp Ser Ser Gly Val Pro Ser Phe Ser Gln
    530                 535                 540

Met Gln Asn Arg Gly Arg Asp Thr Arg Val Glu Phe Trp Ala Phe Asp
545                 550                 555                 560

Leu Leu Tyr Leu Asp Gly Arg Ala Leu Leu Gly Thr Arg Tyr Gln Asp
                565                 570                 575

Arg Arg Lys Leu Leu Glu Thr Leu Ala Asn Ala Thr Ser Leu Thr Val
            580                 585                 590

Pro Glu Leu Leu Pro Gly Asp Gly Ala Gln Ala Phe Ala Cys Ser Arg
        595                 600                 605

Lys His Gly Trp Glu Gly Val Ile Ala Lys Arg Arg Asp Ser Arg Tyr
    610                 615                 620

Gln Pro Gly Arg Arg Cys Ala Ser Trp Val Lys Asp Lys His Trp Asn
625                 630                 635                 640

Thr Gln Glu Val Val Ile Gly Gly Trp Arg Ala Gly Glu Gly Arg
                645                 650                 655

Ser Ser Gly Val Gly Ser Leu Leu Met Gly Ile Pro Gly Pro Gly Gly
```

-continued

```
                660                 665                 670
Leu Gln Phe Ala Gly Arg Val Gly Thr Gly Leu Ser Glu Arg Glu Leu
            675                 680                 685

Ala Asn Leu Lys Glu Met Leu Ala Pro Leu His Thr Asp Glu Ser Pro
        690                 695                 700

Phe Asp Val Pro Leu Pro Ala Arg Asp Ala Lys Gly Ile Thr Tyr Val
705                 710                 715                 720

Lys Pro Ala Leu Val Ala Glu Val Arg Tyr Ser Glu Trp Thr Pro Glu
                725                 730                 735

Gly Arg Leu Arg Gln Ser Ser Trp Arg Gly Leu Arg Pro Asp Lys Lys
            740                 745                 750

Pro Ser Glu Val Val Arg Glu
            755

<210> SEQ ID NO 92
<211> LENGTH: 273
<212> TYPE: PRT
<213> ORGANISM: Mycobacterium tuberculosis

<400> SEQUENCE: 92

Met Arg Ala Ile Trp Thr Gly Ser Ile Ala Phe Gly Leu Val Asn Val
1               5                   10                  15

Pro Val Lys Val Tyr Ser Ala Thr Ala Asp His Asp Ile Arg Phe His
            20                  25                  30

Gln Val His Ala Lys Asp Asn Gly Arg Ile Arg Tyr Lys Arg Val Cys
        35                  40                  45

Glu Ala Cys Gly Glu Val Val Asp Tyr Arg Asp Leu Ala Arg Ala Tyr
    50                  55                  60

Glu Ser Gly Asp Gly Gln Met Val Ala Ile Thr Asp Asp Ile Ala
65                  70                  75                  80

Ser Leu Pro Glu Glu Arg Ser Arg Glu Ile Glu Val Leu Glu Phe Val
                85                  90                  95

Pro Ala Ala Asp Val Asp Pro Met Met Phe Asp Arg Ser Tyr Phe Leu
            100                 105                 110

Glu Pro Asp Ser Lys Ser Ser Lys Ser Tyr Val Leu Leu Ala Lys Thr
        115                 120                 125

Leu Ala Glu Thr Asp Arg Met Ala Ile Val His Phe Thr Leu Arg Asn
    130                 135                 140

Lys Thr Arg Leu Ala Ala Leu Arg Val Lys Asp Phe Gly Lys Arg Glu
145                 150                 155                 160

Val Met Met Val His Thr Leu Leu Trp Pro Asp Glu Ile Arg Asp Pro
                165                 170                 175

Asp Phe Pro Val Leu Asp Gln Lys Val Glu Ile Lys Pro Ala Glu Leu
            180                 185                 190

Lys Met Ala Gly Gln Val Val Asp Ser Met Ala Asp Phe Asn Pro
        195                 200                 205

Asp Arg Tyr His Asp Thr Tyr Gln Glu Gln Leu Gln Glu Leu Ile Asp
    210                 215                 220

Thr Lys Leu Glu Gly Gly Gln Ala Phe Thr Ala Glu Asp Gln Pro Arg
225                 230                 235                 240
```

```
Leu Leu Asp Glu Pro Glu Asp Val Ser Asp Leu Leu Ala Lys Leu Glu
             245                 250                 255
Ala Ser Val Lys Ala Arg Ser Lys Ala Asn Ser Asn Val Pro Thr Pro
             260                 265                 270
Pro
```

PROKARYOTIC DNA REPAIR LIGASES

CROSS-REFERENCE TO RELATED APPLICATIONS

This is a §371 U.S. national stage of International Application No. PCT/GB2004/003349, filed Aug. 2, 2004, which claims the benefit of U.S. Provisional Patent Application No. 60/494,088, filed Aug. 12, 2003. Both applications are incorporated herein in their entirety.

This invention relates to methods and reagents for the manipulation and modification of nucleic acid molecules.

Double-strand breaks (DSBs) in DNA arise during exposure to ionizing radiation (IR) and as intermediates during site-specific rearrangement events such as mating-type switching in Saccharomyces cerevisiae and V(D)J recombination in vertebrates (Critchlow and Jackson (1998) Trends Biochem Sci 23 394). In eukaryotic cells, the primary DNA end-binding component of non-homologous end-joining (NHEJ), Ku, is a heterodimer of two sequence-related subunits (Ku70: 69 kD and Ku80: 83 kD) (Gell & Jackson (1999) Nucl Acid Res 17 3494) that forms an open ringlike structure through which a variety of DNA end structures can be threaded (Walker et al (2001) Nature 412 607). DNA-bound Ku helps to recruit the ligase IV/XRCC4 complex, thereby enhancing its ligation activity (McElhinny et al (2000) Mol. Cell. Biol. 20 2996). In vertebrates, Ku also recruits the DNA-dependent protein kinase catalytic subunit (DNA-PKcs), thereby activating its kinase activity, which is required for DSB rejoining (Dvir et al (1992) PNAS USA 89 11920). Mammalian cells deficient in these NHEJ proteins are defective in DSB rejoining and are hypersensitive to IR (Smith & Jackson (1999) Genes Dev 13 916).

In contrast to the conservation between these components in higher and lower eukaryotes, NHEJ has not been reported in prokaryotes, although genes with homology to Ku70 and Ku80 have been identified in some bacterial genomes (Doherty et al (2001) FEBS Lett 500 186; Aravind & Koonin (2001) Genome Res 11 1365).

The present inventors have identified and characterised a prokaryotic polypeptide that is involved in NHEJ and has a range of enzymatic activities relating to the modification of nucleic acid molecules. These activities are useful in the manipulation of nucleic acid in a range of molecular biology applications.

An aspect of the invention provides a method of modifying a nucleic acid molecule comprising;
contacting the nucleic acid molecule with a prokaryotic DNA repair ligase polypeptide.

A prokaryotic DNA repair ligase polypeptide may comprise an amino acid sequence from a prokaryotic cell which shares greater than about 20% sequence identity with the sequence of Mt-Lig (CAB08492; SEQ ID NO: 91), greater than about 30%, greater than about 40%, greater than about 50%, greater than about 60%, greater than about 70%, greater than about 80%, greater than about 90% or greater than about 95% with the given amino acid sequence.

A prokaryotic ligase may comprise one or more of: a primase domain, a nuclease domain, and a ligase domain. In some embodiments, a prokaryotic ligase may comprise all three domains.

A primase domain may share greater than about 20% sequence identity with the sequence of Mt-Lig (CAB08492; SEQ ID NO: 91) between residues 1-324, greater than about 30%, greater than about 40%, greater than about 50%, greater than about 60%, greater than about 70%, greater than about 80%, greater than about 90% or greater than about 95% with the given amino acid sequence.

A nuclease domain may share greater than about 20% sequence identity with the sequence of Mt-Lig (CAB08492; SEQ ID NO: 91) between residues 325-447, greater than about 30%, greater than about 40%, greater than about 50%, greater than about 60%, greater than about 70%, greater than about 80%, greater than about 90% or greater than about 95% with the given amino acid sequence.

A ligase domain may share greater than about 20% sequence identity with the sequence of Mt-Lig (CAB08492: SEQ ID NO: 91) between residues 448-759, greater than about 30%, greater than about 40%, greater than about 50%, greater than about 60%, greater than about 70%, greater than about 80%, greater than about 90% or greater than about 95% with the given amino acid sequence.

In some embodiments, a prokaryotic DNA repair ligase polypeptide may comprise one or more conserved motifs as shown in FIG. 4 and/or table 2.

Suitable prokaryotic DNA repair ligase polypeptides may include an Mt-lig polypeptide as described below, a B. subtilis YkoU polypeptide, a Bacillus halodurans BH2209 polypeptide, a Pseudomonas aeruginosa PA2150 polypeptide, a Archaeoglobus fulgidus AFI1725 polypeptide, Mesorhizobium loti M112077, M114606, M119625 polypeptides, Sinorhizobium loti SMB20685, SMA0424 polypeptides, Agrobacterium tumefaciens AGR_L_502P and AGR_PAT_68 polypeptides or variants or alleles of these polypeptides.

In some preferred embodiments, the prokaryotic DNA repair ligase polypeptide is an Mt-lig polypeptide. An Mt-lig polypeptide may comprise or consist of the amino acid sequence of database accession number CAB08492 (SEQ ID NO: 91), which is encoded by the M. tuberculosis ORF RV0938 (Z95209) or may be a variant or allele of this sequence.

A gene encoding a prokaryotic DNA repair ligase may be functionally linked with a gene encoding a prokaryotic Ku polypeptide, for example within an operon of the prokaryotic genome.

In some embodiments, a substrate nucleic acid molecule may be contacted with a prokaryotic DNA repair ligase polypeptide in the presence of a prokaryotic Ku polypeptide.

A prokaryotic Ku polypeptide may comprise an amino acid sequence from a prokaryotic cell which shares greater than about 20% sequence identity with the sequence of Mt-Ku (CAB08491; SEQ ID NO: 92), greater than about 30%, greater than about 40%, greater than about 50%, greater than about 60%, greater than about 70%, greater than about 80%, greater than about 90% or greater than about 95% with the given amino acid sequence.

Suitable prokaryotic Ku polypeptides may include Mt-Ku, B. subtilis YkoV, M. Loti Mlr9623, Mlr9624, B. halodurans BH2209 and A fulgidus AF172, or variants or alleles thereof.

In preferred embodiments, the prokaryotic Ku polypeptide is an Mt-Ku polypeptide. An Mt-Ku polypeptide may comprise or consist of the amino acid sequence of database accession number CAB08491 (SEQ ID NO: 92) that is encoded by the M. tuberculosis ORF RV0937c (Z95209) or may be a variant or allele of this sequence.

The production of suitable prokaryotic DNA repair ligases and prokaryotic Ku polypeptides is described in more detail below.

An allele or variant may have an amino acid sequence which differs from a given sequence, by one or more of addition, substitution, deletion and insertion of one or more amino acids but which still has substantially the same sequence as the given sequence. Such an addition, substitution, deletion or insertion may represent a natural variation which occurs between individuals within a species and which has no phenotypic effect. An allele or variant may comprise one or more conserved motifs as shown in FIG. 4 and/or table 2.

A polypeptide which is an amino acid sequence variant or allele may comprise an amino acid sequence which differs from a given amino acid sequence, but which shares greater than about 50% sequence identity with such a sequence, greater than about 60%, greater than about 70%, greater than about 80%, greater than about 90% or greater than about 95%. A variant or allelic sequence may share greater than about 60% similarity, greater than about 70% similarity, greater than about 80% similarity or greater than about 90% similarity with a given amino acid sequence.

Amino acid similarity and identity are generally defined with reference to the algorithm GAP (GCG Wisconsin Package™, Accelrys, San Diego Calif.). GAP uses the Needleman & Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN (which use the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), generally employing default parameters.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine.

Particular amino acid sequence alleles or variants may differ from that a given sequence by insertion, addition, substitution or deletion of 1 amino acid, 2, 3, 4, 5-10, 10-20, 20-30, or 30-50 amino acids A polypeptide for use in a method of the invention may comprise a fragment of a sequence described herein, for example a fragment comprising a primase, nuclease or ligase domain.

A nucleic acid molecule for use in a method of the invention may be linear, with two ends or termini. The ends may independently be blunt-ended or comprise 3' or 5' overhangs.

The nucleic acid molecule may be wholly or partially synthetic and may include genomic DNA, cDNA, RNA or a fragment thereof.

In some preferred embodiments, the nucleic acid molecule is double-stranded. A double-stranded nucleic acid molecule may be modified, for example, by ligating an end of the molecule with an end of either the same or a different nucleic acid molecule, removing 3' overhangs at the ends and filling-in single stranded 'gap' regions.

In other preferred embodiments, the nucleic acid molecule is single-stranded. A single-stranded nucleic acid molecule may be modified, for example, by acting as a template for DNA or RNA polymerase activity to generate a complementary strand Certain preferred embodiments relate to the inter- or intra-molecular ligation of nucleic acid using prokaryotic DNA repair ligase polypeptides.

A method of ligating double-stranded nucleic acid ends may comprise;
    contacting a first nucleic acid end and a second nucleic acid end with a prokaryotic DNA repair ligase polypeptide, such as an Mt-ligase polypeptide.

The first and second nucleic acid ends may be the termini of double stranded nucleic acid molecules, for example, double stranded DNA molecules.

The first and second nucleic acid ends may be on the same nucleic acid molecule (i.e. an intramolecular ligation reaction) or may be on different nucleic acid molecules (i.e. a first and a second nucleic acid molecule joined in an intermolecular ligation reaction).

In some embodiments, one nucleic molecule joined by the prokaryotic DNA ligase may be DNA and the other nucleic acid molecule may be RNA.

For example, a method of joining double-stranded nucleic acid termini may comprise;
    contacting a first nucleic molecule having a first terminus and a second nucleic acid molecule having a second terminus with a prokaryotic DNA repair ligase polypeptide as described above,
    said first and second termini being joined by said polypeptide,
    wherein the first nucleic acid molecule is DNA and the second nucleic acid molecule is RNA.

In some embodiments, the ends or termini to be ligated are non-compatible. Non-compatible ends are non-complementary and therefore non-cohesive. Examples of non-compatible ends include ends created by enzymatic digestion with different restriction endonucleases (i.e. endonucleases-which recognise different nucleotide target sequences). Non-compatible nucleic acid ends may comprise non-complementary single-stranded 5' or 3' overhang regions which do not naturally form base-pairs.

Nucleic acid ends may be contacted with a prokaryotic DNA repair ligase in the presence of a prokaryotic Ku polypeptide as described above. A suitable prokaryotic Ku polypeptide may comprise an amino acid sequence which is naturally associated with the prokaryotic DNA repair ligase, for example a prokaryotic Ku polypeptide from the same strain or species.

A nucleic acid molecule produced by ligation with a prokaryotic DNA repair ligase polypeptide described above may be isolated and/or purified and subjected to further manipulation using standard techniques.

A prokaryotic DNA repair ligase polypeptide, as described above, may also be useful in labelling nucleic molecules by means of a terminal transferase reaction.

A method of labelling a nucleic acid molecule may comprise;
    contacting a nucleic molecule having a first terminus with a prokaryotic DNA repair ligase polypeptide, such as an Mt-lig polypeptide, in the presence of labelled nucleotides.

Labelled nucleotides may be NTPs (i.e. GTP, ATP, TTP, UTP or CTP) or dNTPs (i.e. dGTP, dATP, dTTP, dUTP or dCTP).

A nucleotide may be labelled with a fluorophore such as FITC or rhodamine, a radioisotope, or a non-isotopic labeling reagent such as biotin or digoxigenin.

The DNA dependent RNA or DNA polymerase activity of Mt-lig polypeptide may be useful in filling in gaps (i.e. repairing single stranded regions) in a double stranded nucleic molecule.

A method of filling in a single stranded gap in a double stranded nucleic acid molecule may comprise;
    contacting a double stranded nucleic acid molecule having a single stranded region with a prokaryotic DNA repair ligase polypeptide, such as an Mt-lig polypeptide, in the presence of NTPs or dNTPs.

The nucleic acid molecule may be a DNA molecule and may be linear or circular.

NTPs or dNTPs may be used as substrates for the Mt-ligase polypeptide. A method may be used to fill in a gap in a dsDNA sequence with DNA or with a 'patch' of RNA. This may be useful in a range of applications such as producing DNA substrates with defined labelled patches of DNA or RNA that could be used to study DNA repair, recombination and replication processes using these novel substrates both in vivo and in vivo.

The exonuclease activity of the prokaryotic DNA repair ligase polypeptide may also be useful in blunt ending double stranded nucleic acid and removing single-stranded overhangs.

A method of blunt-ending a nucleic acid molecule may comprise;

contacting said nucleic acid molecule comprising a single stranded overhang with a prokaryotic DNA repair ligase polypeptide.

The nucleic acid molecule may contacted with the prokaryotic DNA repair ligase polypeptide in the presence of Mg2+ or Mn2+.

The overhang may be a 3' overhang.

A suitable prokaryotic DNA repair ligase polypeptide for use in blunt ending methods may comprise or consist of a prokaryotic DNA repair ligase nuclease domain as described above.

DNA dependent RNA polymerase-activity of a prokaryotic DNA repair ligase polypeptide as described above may be used to produce RNA molecules.

A method of producing an RNA molecule may comprise;

contacting a prokaryotic DNA repair ligase polypeptide, such as an Mt-lig polypeptide and a template DNA strand in the presence of NTPs.

Prokaryotic DNA repair ligase polypeptides are shown herein to possess an RNA primase activity which allows RNA to be synthesised without a primer sequence. In other embodiments, a primer may be desirable and the prokaryotic DNA repair ligase polypeptide and template DNA may be contacted in the presence of a primer oligonucleotide.

The RNA strand synthesised by the prokaryotic DNA repair ligase polypeptide may be isolated and/or purified, for example from the template DNA by reverse phase liquid chromatography or digestion with a DNA nuclease.

The DNA polymerase activity of a prokaryotic DNA repair ligase polypeptide may be used to produce a DNA molecule.

A method of producing an DNA molecule may comprise;

contacting a prokaryotic DNA repair ligase polypeptide and a template nucleic acid strand in the presence of dNTPs and a primer oligonucleotide.

Prokaryotic DNA repair ligase polypeptides such as Mt-lig polypeptide are shown herein to possess a DNA dependent DNA polymerase activity and an RNA dependent DNA polymerase (i.e. reverse transcriptase). Suitable template nucleic acid strand may therefore be either DNA or RNA.

Other aspects of the invention relate to kits and reagents for use in molecular-biology applications.

A composition for use in a method described above may comprise an isolated prokaryotic DNA repair ligase polypeptide, for example a Mt-lig polypeptide, and an isolated prokaryotic Ku polypeptide, such as Mt-Ku. The composition may further comprise buffers, stabilisers, excipients, $Mg^{2+}$ and/or $Mn^{2+}$. A composition may also comprise dNTPs or NTPs.

Reagents for use in a method as described herein, such as isolated prokaryotic DNA repair ligase polypeptide, may be provided as part of a kit, e.g. in a suitable container such as a vial in which the contents are protected from the external environment. In preferred embodiments, the kit also comprises an Mt-Ku polypeptide as described above. The kit may include instructions for use of the polypeptide e.g. in a method described above. A kit may include one or more other reagents required for the method, such as buffers, excipients, stabilisers, NTPS, dNTPs, labelled NTPs/dNTPs, $Mg^{2+}$ or $Mn^{2+}$. A kit may also include vessels such as tubes or curvettes suitable for use in carrying out the method.

Another aspect of the invention provides a kit comprising an isolated prokaryotic DNA repair ligase polypeptide such as Mt-lig polypeptide and, optionally an isolated prokaryotic Ku polypeptide, such as Mt-Ku, for use in a method of modifying a nucleic acid molecule as described above.

Other aspects of the invention relate to the production of prokaryotic DNA repair ligase polypeptides such as Mt-lig polypeptide.

A method of producing a prokaryotic DNA repair ligase polypeptide may comprise;

(a) causing expression from nucleic acid which encodes a prokaryotic DNA repair ligase polypeptide in a suitable expression system to produce the polypeptide recombinantly;

(b) testing the recombinantly produced polypeptide for prokaryotic DNA repair ligase polypeptide activity.

Prokaryotic DNA repair ligase polypeptide activity may include one or more of the following: non-complementary end ligation activity, DNA dependent RNA primase activity, 3'-5' exonuclease activity, DNA and RNA dependent DNA polymerase activity, DNA dependent RNA polymerase activity, ATP dependent DNA and RNA ligase activity and DNA terminal transferase activity.

Determination of one or more of these activities may be performed using standard techniques in the art (for example, see Sambrook & Russell, Molecular Cloning, A Laboratory Manual, Cold Spring Harbor Laboratory Press, 2001, and Ausubel et al, Short Protocols in Molecular Biology, John Wiley and Sons, 1992).

Suitable prokaryotic DNA repair ligase polypeptides are described above and include a *B. subtilis* YkoU polypeptide, a *Bacillus halodurans* BH2209 polypeptide, a *Pseudomonas aeruginosa* PA2150 polypeptide, a *Archaeoglobus fulgidus* AFI1725 polypeptide, *Mesorhizobium loti* M112077, M114606, M119625 polypeptides, *Sinorhizobium loti* SMB20685, SMA0424 polypeptides, *Agrobacterium tumefaciens* AGR_L_502P and AGR_PAT_68 polypeptides, Mt-Lig and variants or alleles of these polypeptides.

Methods for the production of a recombinant polypeptide from encoding nucleic acid are well known in the art. Nucleic acid sequences encoding a Mt-lig polypeptide may be readily prepared by the skilled person using the information and references contained herein and techniques known in the art (for example, see Sambrook & Russell, Molecular Cloning, A Laboratory Manual, Cold Spring Harbor Laboratory Press, 2001, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from the *M. tuberculosis* genome, (ii) chemical synthesis, or (iii) preparing cDNA sequences. DNA encoding Mt-lig polypeptides may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers.

In order to obtain expression of nucleic acid sequences, the sequences can be incorporated in a vector having one or more control sequences operably linked to the nucleic acid to control its expression. The vectors may include other sequences such as promoters or enhancers to drive the expression of the inserted nucleic acid, and/or nucleic acid sequences so that the polypeptide or peptide is produced as a fusion. Polypeptide can then be obtained by transforming the vectors into host cells in which the vector is functional, culturing the host cells so that the polypeptide is produced and recovering the polypeptide from the host cells or the surrounding medium. Prokaryotic cells are used for this purpose in the art, including strains of E. coli. The protein may also be expressed using the eukaryotic insect cell baculovirus expression system.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 3rd edition, Sambrook et al. (2001) Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Following production, a polypeptide may be isolated and or purified using standard techniques.

Other aspects of the invention provide an isolated nucleic acid comprising a nucleotide sequence encoding a prokaryotic DNA repair ligase polypeptide as described above operably linked to a heterologous regulatory element, an expression vector comprising such a nucleic acid and a host cell, for example a prokaryotic host cell such as an E. coli cell, comprising such an expression vector.

An isolated nucleic acid comprising a nucleotide sequence encoding a prokaryotic DNA repair ligase polypeptide may further comprise a nucleotide sequence encoding a prokaryotic Ku polypeptide that is operably linked to a heterologous regulatory element.

Prokaryotic DNA repair ligase polypeptides, prokaryotic Ku polypeptides and encoding nucleic acids are described in more detail above.

Regulatory elements, expression vectors and host cells suitable for the expression of an Mt-lig polypeptide or other prokaryotic DNA repair ligase polypeptide are well-known in the art.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described below.

Figure 1:
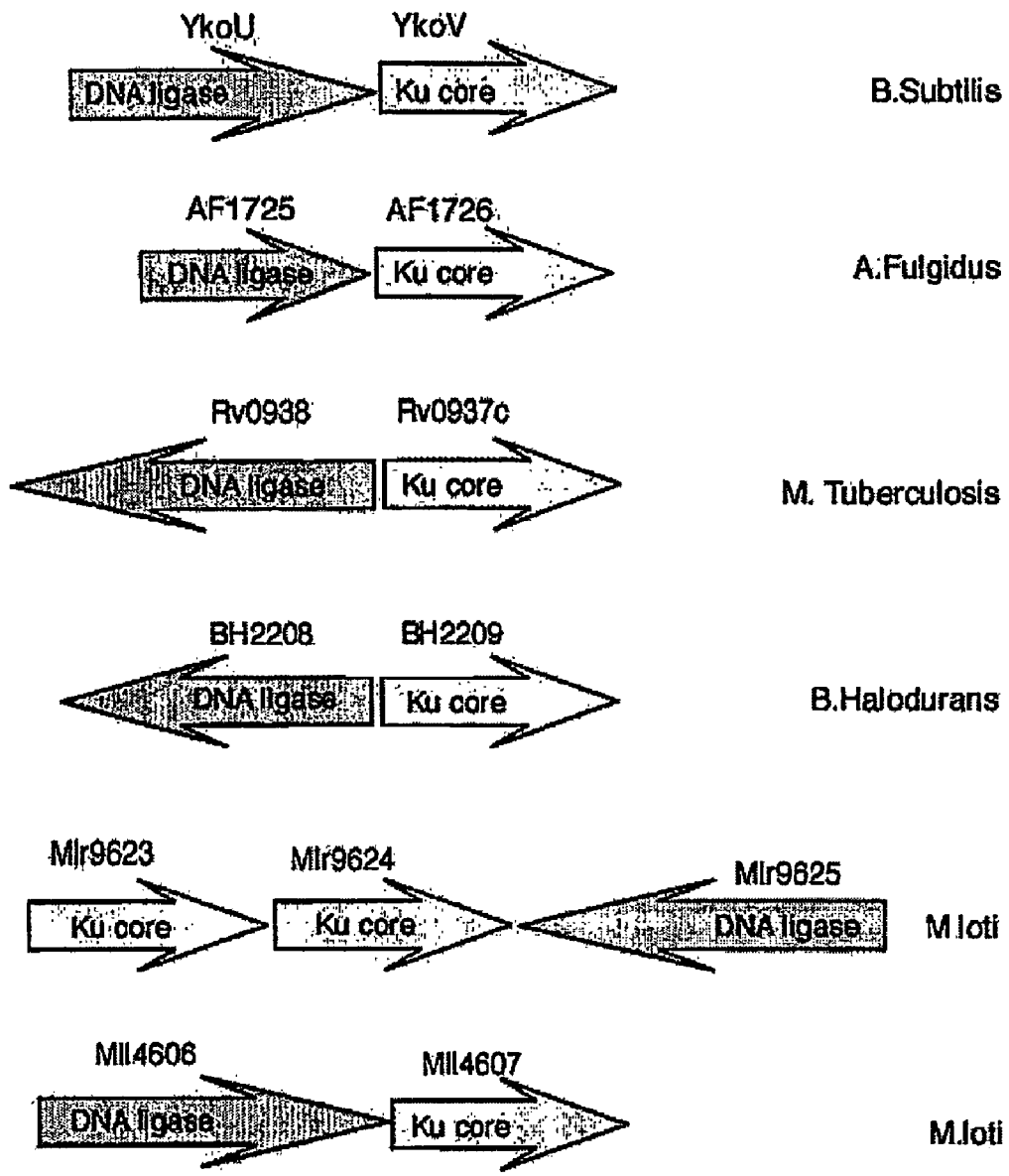
FIG. 1 shows the arrangement of the DNA ligase and Ku genes in the Ku-like gene operon in of various prokaryotes.
Figure 2:
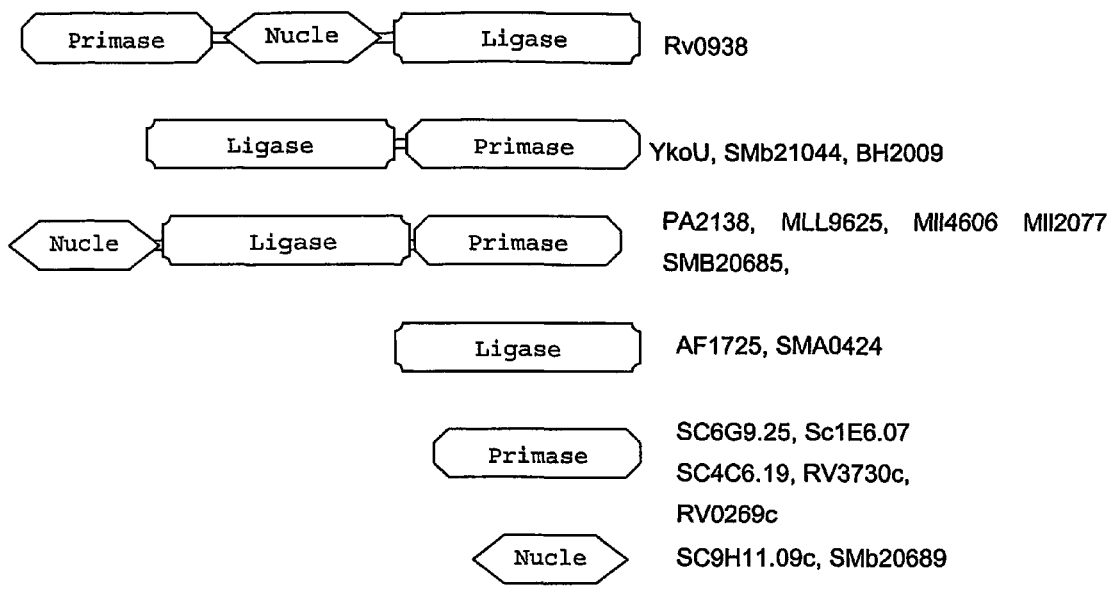
FIG. 2 shows the domain structure of a variety of prokaryotic DNA repair ligases.
Figure 3:
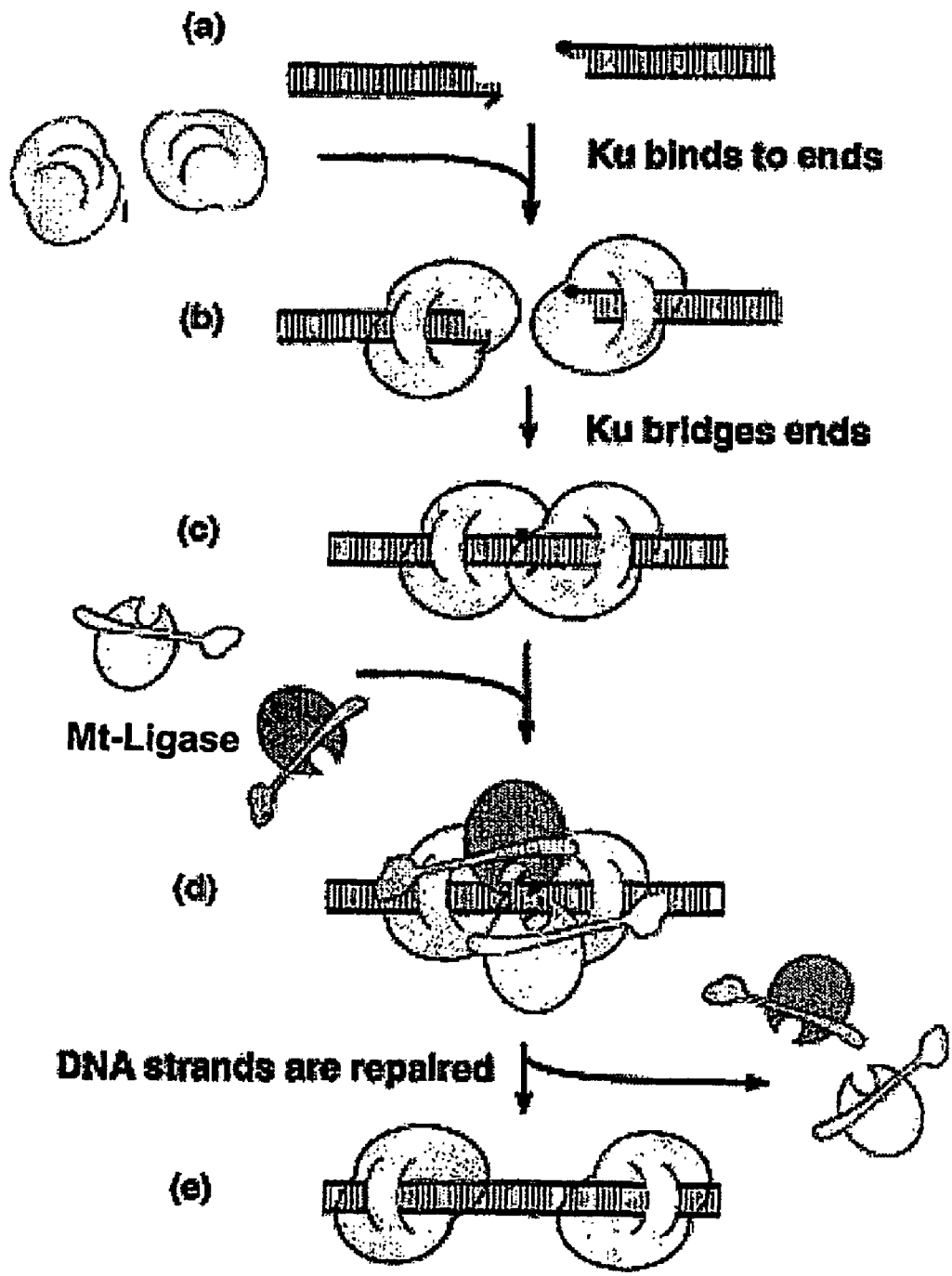
FIG. 3 shows a putative mechanism for Mt-Lig and Mt-Ku.
Figure 4:
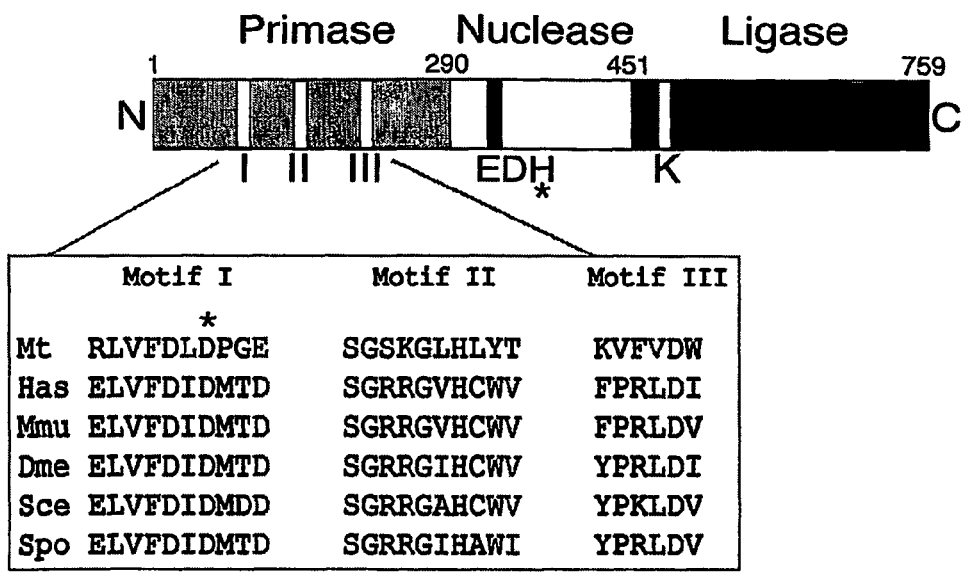

FIG. 4 shows the Mt-Lig gene with the principle catalytic domains indicated (primase domain 1-324, nuclease domain 325-447 and ligase domain 448-759). I represents conserved motif: RLVFDLDPGE (SEQ ID NO: 1), II represents SGSKGLHLYT (SEQ ID NO: 2) and III represents KVFVDW (SEQ ID NO: 3). Variants of motif I include RLVFDLDPGE (SEQ ID NO: 72); ELVFDIDMTD (SEQ ID NO: 75); and ELVFDIDMDD (SEQ ID NO: 81). Variants of motif II include SGSKGLHLYT (SEQ ID NO: 73); SGRRGVHCWV (SEQ ID NO: 76) SGRRGIHCWV (SEQ ID NO: 79); SGRRGAHCWV (SEQ ID NO: 82); and SGRRGIHAWI (SEQ ID NO: 84). Variants of motif III include KVFVDW (SEQ ID NO: 74); FPRLDI (SEQ ID NO: 77); FPRLDV (SEQ ID NO: 78); YPRLDI (SEQ ID NO: 80); YPKLDV (SEQ ID NO: 83); and YPRLDV (SEQ ID NO: 85).

Figure 5:
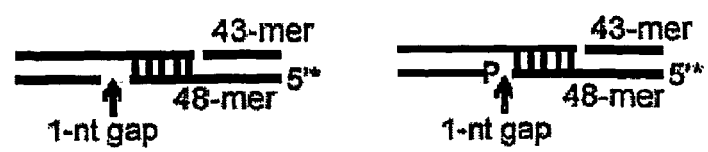
Figure 5:
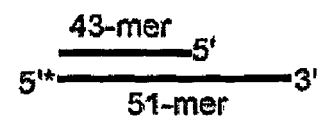
Figure 5:
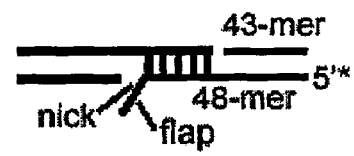

FIG. 5 shows constructs used to assay the activities of Mt-Ligase in the experiments described herein. FIG. 5(A) left panel shows a DNA duplex that forms a non-ligatable one nucleotide gap which is efficiently filled by Mt-Lig. FIG. 5(A) right panel shows a DNA duplex having a phosphate group added to the 5' terminus at the gap.

FIG. 5(B) shows a DNA duplex construct with a 3'-overhang.

FIG. 5(C) shows a DNA duplex construct containing non-ligatable one nucleotide gaps and a single stranded flap region.

Figure 6:
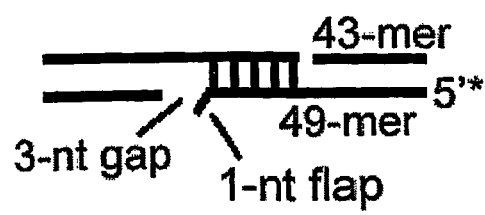
Figure 6:
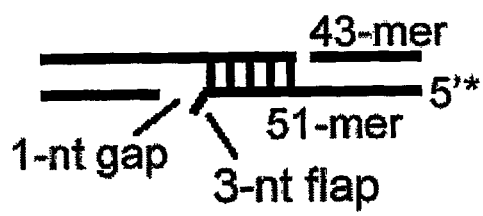
Figure 6:
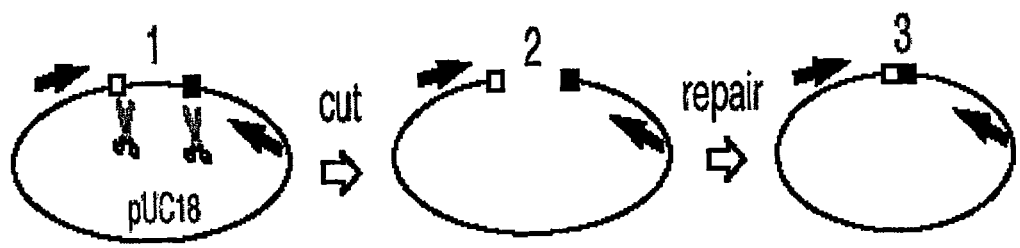

FIG. 6 shows constructs used in assays for joining of DNA molecules with incompatible ends by Mt NHEJ.

FIGS. 6(A) and FIG. 6(B) show DNA duplexes for assaying Mt-Lig activity.

FIG. 6(C) shows a schematic of a plasmid repair assay, as described herein.

Figure 7:
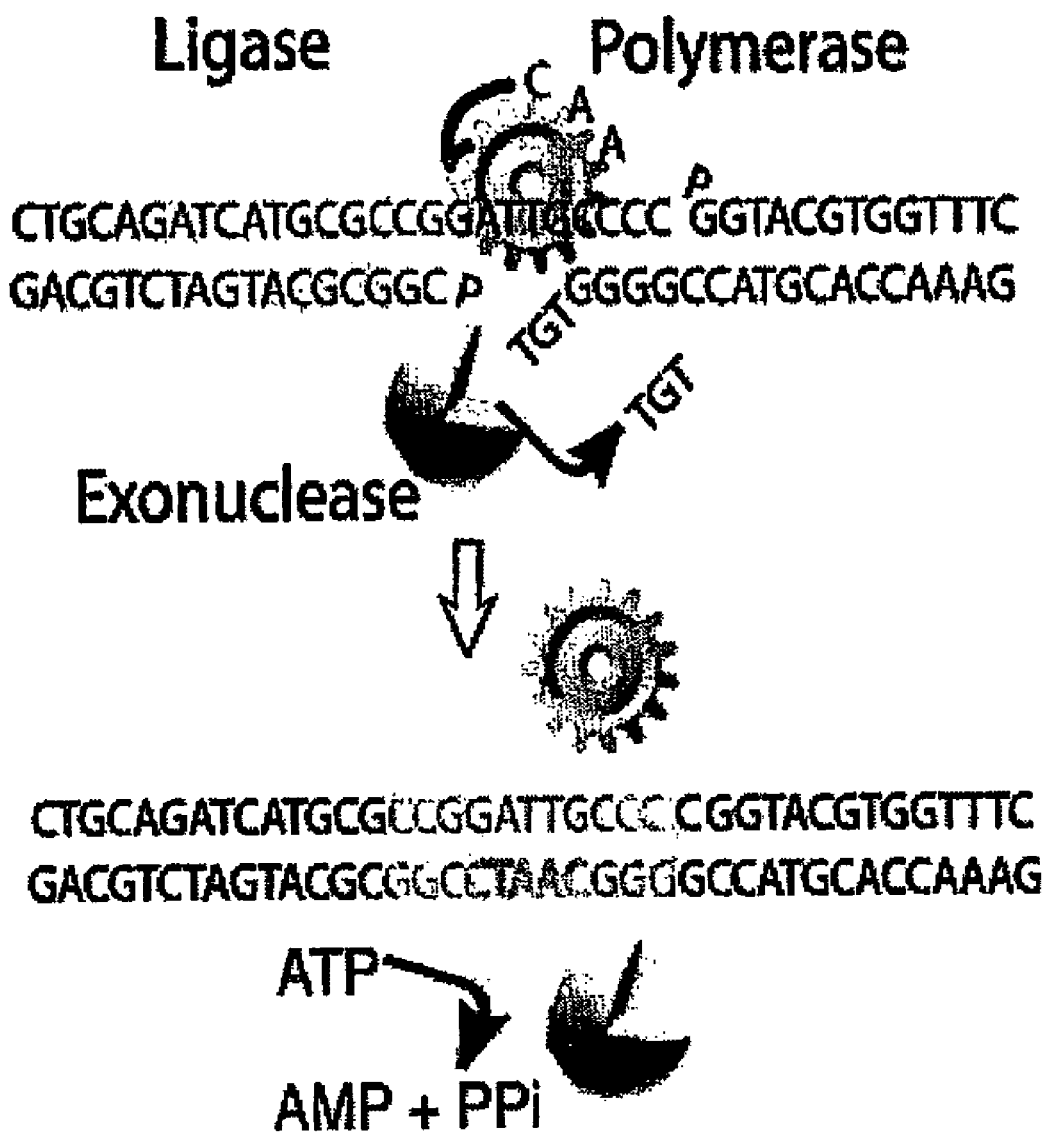

FIG. 7 shows a schematic of the interaction of the nuclease, polymerase and ligase activities of Mt-Lig in NHEJ. The sequences shown are CTGCAGATCATGCGCCGGATTGC-CCC (SEQ ID NO: 20); GGTACGTGGTTTC (SEQ ID NO: 86); CGGCGCATGATCTGCAG (SEQ ID NO: 87); GAAACCACGTACCGGGGTGT (SEQ ID NO: 88); CTG-CAGATCATGCGCCGGATTGCCCCGGTACGTGGTTTC (SEQ ID NO: 89); and GAAACCACGTAC-CGGGGCAATCCGGCGCATGATCTGCAG (SEQ ID NO: 90).

Figure 8:
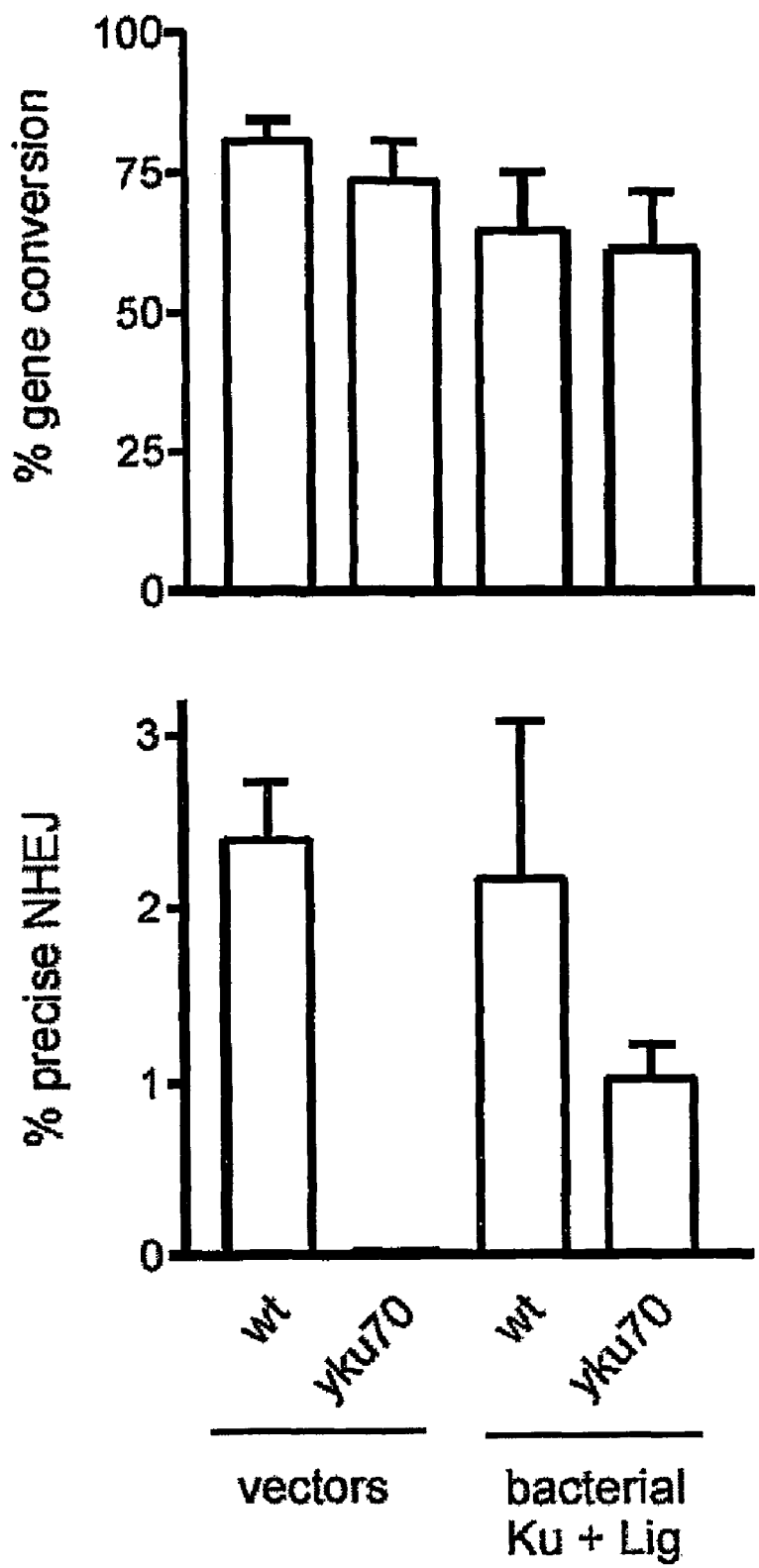

FIG. 8 shows the frequencies of gene conversion and simple religation NHEJ in wild-type and yku70 mutant yeast demonstrating reconstitution of NHEJ by combined expression of Mt-Ku and Mt-Lig.

Figure 9:
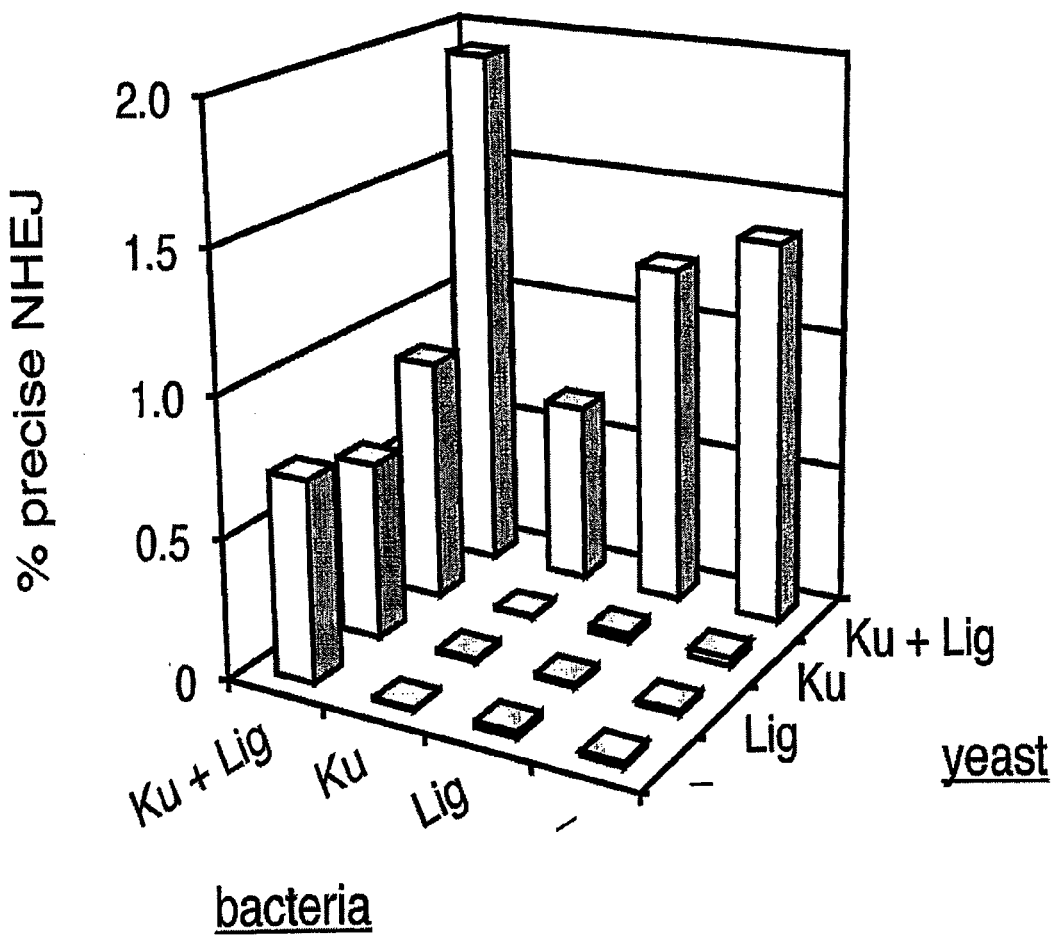

FIG. 9 shows combinations of yeast and Mt Ku and ligase genes tested for NHEJ function in the absence of the gene conversion donor. Labels indicate those functions that were present in the cell. For example, "yeast Lig" indicates the strain genotype yku70 DNL4, while "bacteria Ku" indicates the presence of only the Mt-Ku expression plasmid.

Figure 10:
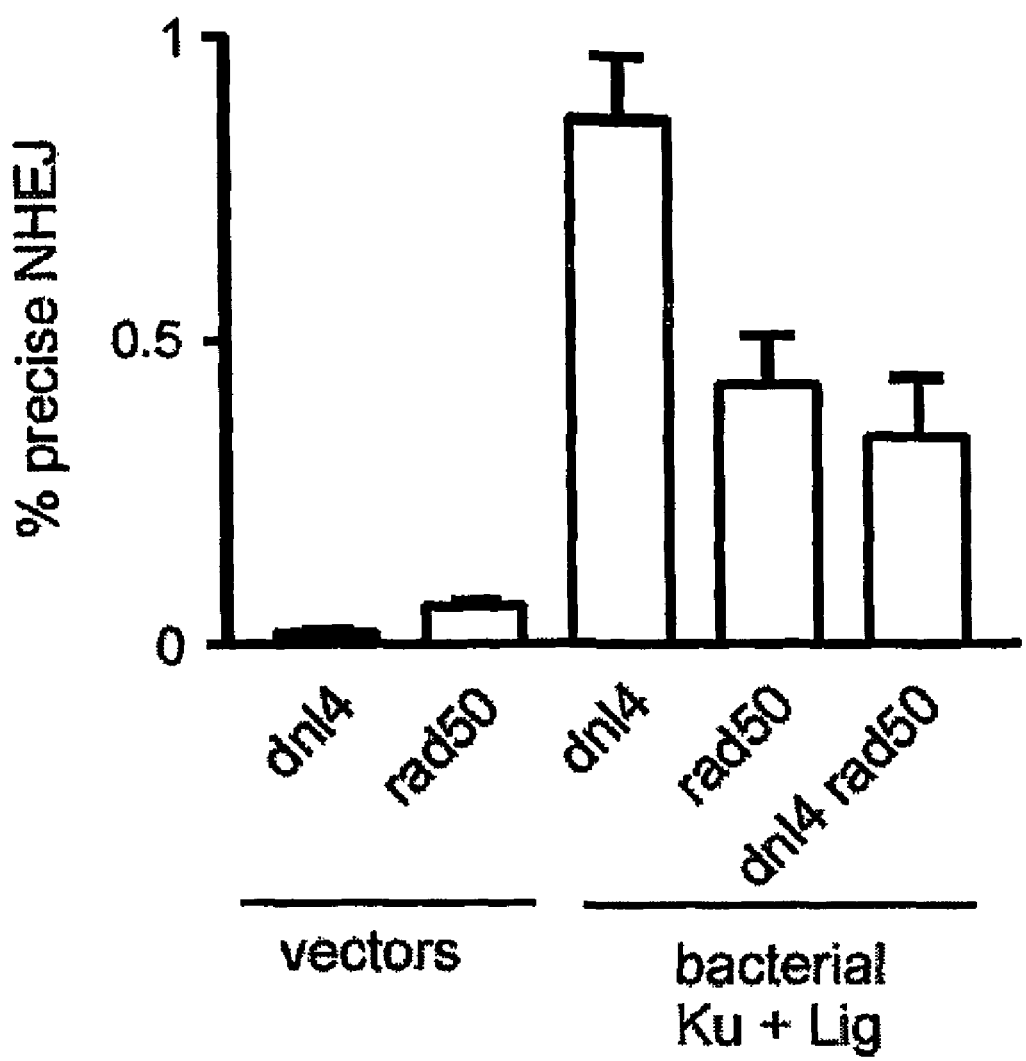

FIG. 10 shows that NHEJ catalyzed by Mt proteins in yeast is only partially dependent on an intact MRX complex. No Ade+ colonies were recovered from dn14 rad50 yeast with vectors only and so this combination is not plotted.

Figure 11:
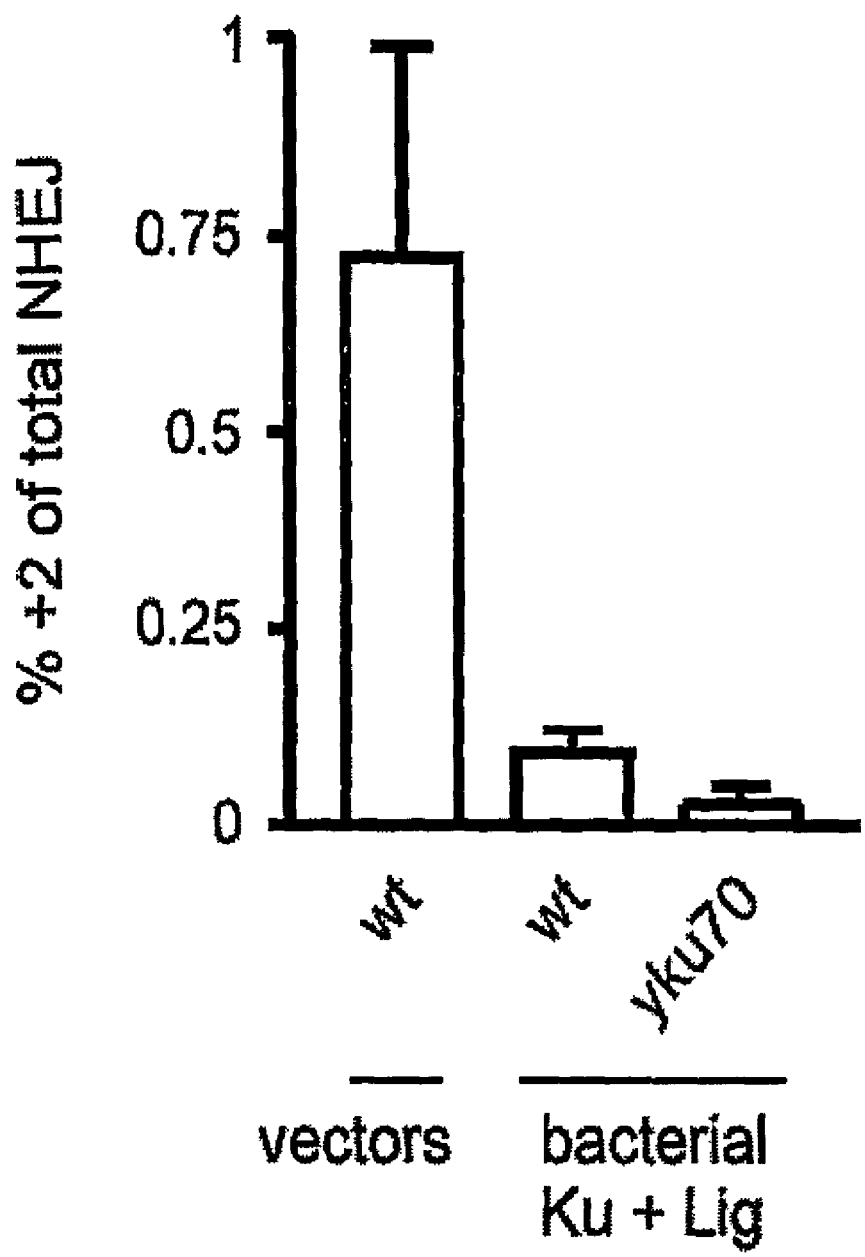

FIG. 11 shows the extent of +2 frame-shifted NHEJ determined as a fraction of the total NHEJ events. Mt NHEJ led to a markedly lower +2 frequency than did yeast NHEJ, even in wild-type yeast. No Ade+ colonies were recovered from yku70 yeast with vectors only and so this strain is not plotted.

FIG. 12 shows diagrams of the inferred NHEJ intermediates for the HO(+2) and HO(−1) events, the overhang-to-overhang NHEJ events that will give a +2 reading frame.

Figure 13:
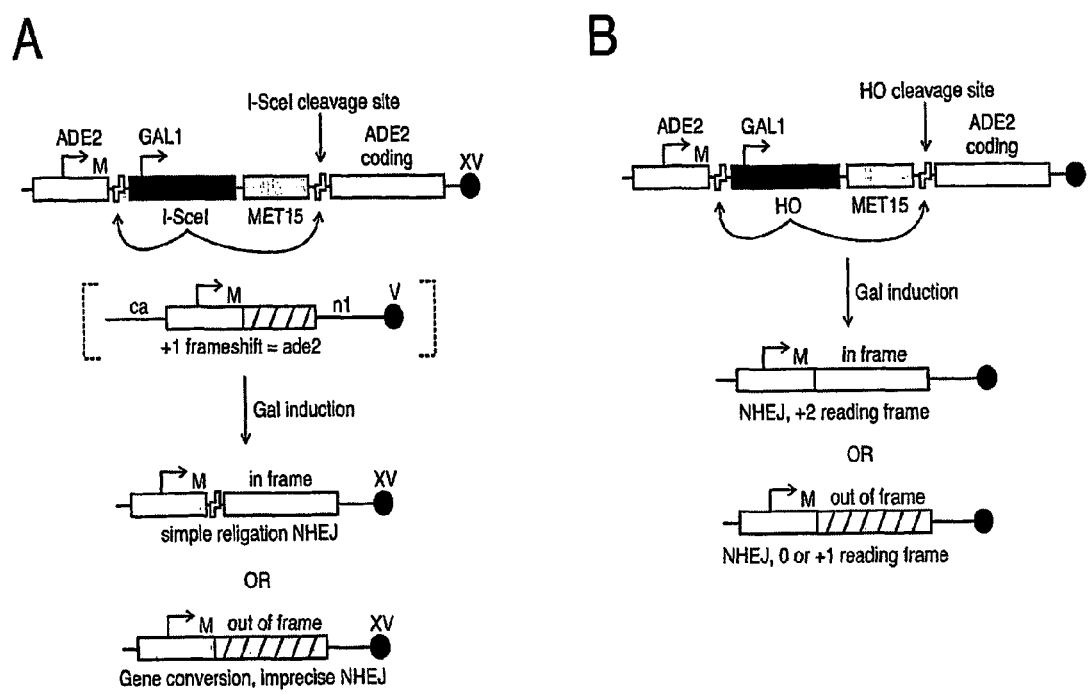

FIG. 13 shows schematics of the suicide deletion systems used herein.

FIG. 13(A) shows a system in which galactose induction leads to I-SceI-mediated cleavage of its gene cassette from chromosome XV. Repair of the resulting DSB by precise religation NHEJ leads to in-frame expression of the ADE2 reporter gene. Imprecise NHEJ or, when present, gene conversion with a frame-shifted ade2 fragment on chromosome V leads to an out-of-frame ade2 gene on chromosome XV.

FIG. 13(B) shows a similar system to that of FIG. 13(A), except using the HO endonuclease and no gene conversion donor. Also, the initial reading frame has been adjusted so that precise simple-religation NHEJ (i.e. a frame-shift of 0 relative to an intact HO cut site) yields an out-of-frame ade2 product, while imprecise NHEJ events that result in a +2 frame-shift (or equivalent) yield an in-frame ADE2 product.

Table 1 shows sequences of plasmids from plasmid rescue assays, which were transformed into bacteria and subsequently sequenced. The starting ends, final products, and inferred alignment intermediates are shown.

Table 2 shows the conserved regions of prokaryotic ligases.

EXAMPLES

Materials and Methods

Cloning of Rv0937c and Rv0938 ORFs.

Full-length sequences for *M. tuberculosis* Rv0937c and Rv0938 were amplified by PCR from H37Rv genomic DNA using the following primers:

Rv0937c (*M. tuberculosis* Ku, 274 amino acids, 30.9 kD) was amplified using 5' primer (5'-ATG CGA GCC ATT TGG ACG GG-3') (SEQ ID NO: 4) and 3' primer (5'-GGA TCC TCA CGG AGG CGT TGG GAC G-3') (SEQ ID NO: 5).

Rv0938 (*M. tuberculosis* ligase, 759 amino acids, 83.6 kD) was amplified using 5' primer (5'-ATG GGT TCG GCG TCG GAG CA-3') (SEQ ID NO: 6) and 3' primer (5'-TCC TCA TTC GCG CAC CAC CTC ACT GG-3') (SEQ ID NO: 7).

The 5' primers contained an Nde I site, and the 3' primers contained a Bam HI site. PCR products were cloned into pET16b (Novagen). All DNAs cloned from PCR products were sequenced to confirm that no mutations were introduced during PCR. Proteins over-expressed from this vector carry an extra 21 amino acids (2.5 kD) at the NH2-terminus of the protein, due to addition of a 10-His tag and a Factor Xa cleavage site.

Overexpression of RV0937c and RV0938.

Recombinant protein was produced by first transforming *E. coli* B834 (DE3) pLysS cells (Novagen) with the pET16b plasmid (containing either Rv0938 or Rv0937c) and then selecting a single colony which was grown overnight at 37° C. in 5 ml LB broth supplemented with ampicillin at 100 µg/ml and chloramphenicol at 34 µg/ml. The overnight culture was used to inoculate 1 liter of LB broth supplemented with ampicillin and chloramphenicol as before. This culture was grown at 37° C. until an OD600 of 0.6 was achieved. At this point the culture was removed from the incubator and cooled to room temperature in a water bath and IPTG was added to a final concentration of 0.5 µM, to induce the production of the recombinant protein.

The culture was then returned to the incubator and grown overnight at 28° C. The cells were pelleted for 20 min at 4000 g.

Purification of Mt-Ku (RV0937c)

After sonication, the cell supernatant was treated with 60% of a saturated ammonium sulfate solution, incubating on ice for 1 hour. This was spun down, and the pellet was carefully resuspended in buffer A (50 mM Tris pH 7.5, 60 mM NaCl, 30 mM imidazole, 17 µg/ml PMSF, 34 µg/ml benzamidine). The resuspended was then loaded onto a nickel agarose (Qiagen) column, washed with 60 mM imidazole, and the protein eluted with 300 mM imidazole. The 300-mM peak was then loaded onto a DEAE Sepharose fast flow column. The Ku protein eluted between 200 and 300 mM NaCl.

Purification of Mt-Lig (RV0938)

After sonication, the cell debris was removed by centrifugation. The supernatant pellet was then loaded onto a nickel agarose column (Qiagen), washed with 60 mM imidazole, and the protein eluted with 300 mM imidazole. The 300 mM peak was then loaded onto a 5 ml Hi-Trap Q-Sepharose column (Amersham Biosciences). The ligase eluted at around 300 mM NaCl, which corresponded to a single protein band at approximately 83 kD, the predicted size for the full length Rv0938 gene product.

Double-Stranded Ligation Assay

Equimolar concentrations of Mt-Lig, Ligase IV/XRCC4 or T4 DNA ligase were incubated for 2 hours in 30 µl reaction mixture (50 mM Triethanolamine, pH 7.5, 2 mM Mg(OAc)2, 2 mM DTT, 0.1 mg/ml BSA) or 1× reaction buffer for T4 DNA ligase (Roche) with 70 fmol of DNA ([γ-32P]ATP labelled on the 5' end). Double-stranded DNA fragments were produced from the Bluescript plasmid (Stratagene) to give substrates of 53 bp, and 445 bp, and 2.56 kbp with 4 bp overhangs at each end, and a 157-bp substrate with a 4-bp and a 2-bp overhang. These cohesive ends were not complementary to limit circularization. Bluescript was digested initially with the restriction enzymes Pst I and Afl III (NEB) to produce the 445-bp and 2.56-kbp DNA fragments. The large fragment produced by the first digestion was subjected to a second double digest with Kpn I and Pvu II (NEB) to produce 53 bp and 157 bp fragments.

After incubation, the reactions were deproteinized, phenol/chloroform extracted and precipitated with Pellet-Paint co-precipitant (Novagen). Aliquots of the reactions were run on 0.8% agarose gels. Dried gels were analyzed and quantified using a STORM PhosphorImager (Molecular Dynamics). Reactions with Ku heterodimer were preincubated for 15 min on ice with indicated amounts of Ku heterodimer, and ligation reaction was started by adding the enzyme and transfer to 37° C.

DNA and RNA Extension Assays

Equal amounts of the labelled and unlabelled oligonucleotides were annealed by incubation at 70° C. for 10 min, 50° C. for 10 min, 40° C. for 10 min, 18° C. for 10 min, and then on ice for 5 min, to generate a linear duplex with the desired nucleotide gap using the following pairs of oligonucleotides; 5'-$^{32}$P labelled 15-mer (5'-CTGCAGCTGATGCGC-3') (SEQ ID NO: a) annealed to 20-mer (5'ATCCGGCGCATCAGCT-GCAG-3') (SEQ ID NO: 9); 5'-$^{32}$P labelled 15-mer (5'-CTG-CAGCT-GATGCGC-3') (SEQ ID NO: 8) annealed to 25-mer (5'-AGTCGATCCTGCGCATCATCTGCAG-3') (SEQ ID NO: 10); 5'-$^{32}$P labelled 15-mer (5'-CTGCAGCTGAT-GCGC-3') (SEQ ID NO: 8) annealed to 41-mer (5'-AC-CCGGGGATCCGTACAGTCTATCCGGCG-CATCAGCTGCAG-3') (SEQ ID NO: 11).

Alignment of the complementary single strands generates a non-ligatable nick in the unlabelled strand and a single-nucleotide gap in the labelled strand. A similar strategy was used to construct pairs of duplexes with single-strand extensions that, when aligned, give differently sized gaps with and without single-strand flaps.

The duplexes (100 nM) were incubated with Mt-ligase as indicated in reaction mixtures (10 µl) containing 50 mM potassium acetate, 20 mM Tris-acetate, 10 mM magnesium acetate, 1 mM dithiothreitol, pH 7.9 @25° C., 0.05 mM of each of the four dNTPs or the four NTPs. The reactions were supplemented with 100 µg/ml BSA and incubated at 37° C. for 30 min.

The reactions were stopped by the addition of gel loading buffer (95% (v/v) formamide, 0.09% (w/v) bromphenol blue, and 0.09% (w/v) xylene cyanol). After separation by denaturing gel electrophoresis, labelled DNA molecules in the dried gel were detected and quantitated by Phosphor-Imager analysis or x-ray exposure.

Ligation of Breaks Assay

Linear duplexes with complementary single-strand ends were constructed by annealing pairs of oligonucleotides. Alignment of the complementary single strands generates a ligatable nick in both the unlabelled and labelled strand and a single-nucleotide gap in the labelled strand. A similar strategy was used to construct pairs of duplexes with single-strand extensions that, when aligned, give differently sized gaps with and without single-strand flaps. Equal amounts of the labelled and unlabelled duplexes (100 nM) were incubated with Mt-ligase in 50 mM Tris-HCl, 10 mM MgCl2, 10 mM DTT, 1 mM ATP, 25 µg/ml BSA, (pH 7.5 @ 25° C.), 0.05 mM of each of the four dNTPs or the four NTPs. The reaction was incubated at 37° C. for 30 min. In assays to measure both DNA synthesis and ligation, the 5' termini of unlabelled oligonucleotides were phosphorylated.

Terminal Transferase Assay

Reaction mixtures (10 µl) containing 25 mM Tris-HCl (pH 7.5), 10 mM MgCl$_2$, 1 mM DTT, 100 µg/ml BSA, 100 nM 5'-$^{32}$P labeled 50mer substrate (5'-GTA ACA AAG TTT GGA TTG CTA CTG ACC GCT CTC GTG CTC GTC GCT GCG TT-3') (SEQ ID NO: 12), 3 µg Mt-lig, and, as indicated, 50 µM ATP or 50 µM dATP. Reactions were incubated at 25° C. for 2 h and terminated by the addition of 1 µl loading buffer. After heat denaturation at 90° C. for 2 min, 4 µl of each reaction was loaded onto a 10% polyacrylamide-8M urea gel. After separation by electrophoresis, labelled products were detected by phosphor-imager analysis.

Primase Assay

Reaction mixtures (10 µl) contained 25 mM Tris-HCl (pH 7.5), 10 mM MgCl$_2$, 1 mM DTT, 100 µg/ml BSA, 0.25 µg of M13mp19 (Invitrogen), 0.25 µCi [α-$^{32}$P] ATP, various amounts of Mt-Lig, and, as indicated, 50 µM each of either GTP, CTP and UTP or 50 µM dNTPs. Reactions were incubated at 25° C. for 2 h and terminated by the addition of 1 µl loading buffer (95% formamide, 0.03% each bromophenol blue and xylene cyanol). After heat denaturation at 90° C. for 2 min, 4 µl of each reaction was loaded onto a 15% polyacrylamide-8M urea gel. After separation by electrophoresis, labelled products were detected by phosphor-imager analysis.

Coupled DNA Synthesis and Ligation

Linear duplexes with complementary single strand ends were constructed by annealing the following pairs of oligonucleotides; 5'-$^{32}$P labelled 50-mer (5'-GTC TGT CTC ACT ATT AGA ACC CTT TAG AGT CAT GCG TCG CGA GGC AAC GC-3') (SEQ ID NO: 13) annealed to 43-mer (5'-GCC TCG CGA CGC ATG ACT CTA AAG GGT TCT AAT AGT GAG ACA G-3') (SEQ ID NO: 14); 41-mer (5'-GCG ACG AGC ACG AGA GCG GTC AGT AGC AAT CCA AAC TTT GT-3') (SEQ ID NO: 15) annealed to 50-mer (5'-GTA ACA AAG TTT GGA TTG CTA CTG ACC GCT CTC GTG CTC GTC GCT GCG TT-3') (SEQ ID NO: 16). Equal amounts of labelled and unlabeled duplexes (100 nM of each) were incubated with various amounts of Mt-Lig in reaction mixtures (10 µl) containing 25 mM Tris-HCl (pH 7.5), 10 mM MgCl$_2$, 50 µM each of dNTPs and 1 mM ATP at 25° C. for 2 h.

Reactions were terminated by the addition of 1 µl loading buffer. After heat denaturation at 90° C. for 2 min, 4 µl of each reaction was loaded onto a 10% polyacrylamide-8M urea gel. After separation by electrophoresis, labelled products were detected by phosphor-imager analysis.

Nuclease Assay

Linear duplexes with complementary single-strand ends were constructed by annealing pairs of oligonucleotides; 5'-$^{32}$P labeled 524-mer (5'-CTG TCT GTC TCA CTA TTA GAA CCC TTT AGA GTC ATG CGT CGC GAG GCA ACG C-3') (SEQ ID NO: 17) annealed to 43-mer; 41-mer annealed to 50-mer. 5'-$^{32}$P labelled 20-mer (5'-GAAACCACGTAC-CGGCGTGT-3') (SEQ ID NO: 18) annealed to 13mer (5'-CTTTGGTCGATGG-3') (SEQ ID NO: 19); 26mer (5'-CTG-CAGATCATGCGCCGGATTGCCCC-3') (SEQ ID NO: 20) annealed to 17-mer (5'-GACGTCTAGTACGCGGC-3) (SEQ ID NO: 21). Alignment of the complementary single strands generates a ligatable nick in both the unlabelled and labelled strand and a single-nucleotide gap in the labelled strand. A similar strategy was used to construct pairs of duplexes with single-strand extensions that, when aligned, give differently sized gaps with and without single-strand flaps. Equal amounts of the labelled and unlabelled duplexes (100 nM) were incubated with Mt-ligase in 50 mM potassium acetate, 20 mM Tris-acetate, 10 mM magnesium acetate, 1 mM dithiothreitol, pH 7.9 @ 25° C. The reactions were supplemented with 100 µg/ml BSA and incubated at 37° C. for 30 min. The reactions were stopped by the addition of gel loading buffer (95% (v/v) formamide, 0.09% (w/v) bromphenol blue, and 0.09% (w/v) xylene cyanol). After separation by denaturing gel electrophoresis, labelled DNA molecules in the dried gel were detected and quantitated by Phosphor-Imager analysis or x-ray exposure. In assays to measure both DNA synthesis and ligation, the 5' termini of unlabelled oligonucleotides were phosphorylated.

Plasmid Repair Assays pUC18 plasmid was cut with restriction enzymes to give different non-complementary overhangs, producing a linearised duplex approximately 400-600 bp smaller than the uncut plasmid. SmaI and AatII were used to give a blunt end and a 3' overhang, HindIII and EcoRI were used to give non-complementary 5' overhangs, cut plasmid was purified using the Qiagen gel extraction kit. The plasmid was cut in such a way as to remove a 400-600 bp region from the plasmid. The reactions were carried out in 20 ul, with T4 ligase buffer (NEB), 50 uM dNTPs or NTPs, 50 nmol of cut plasmid, with Mt ligase (4 pmol) and Mt-Ku (0.05, 0.1, 0.5, or 1 pmol) as indicated. For controls, T4 ligase (0.2 units). The reactions were incubated with Mt ku for 20 minutes on ice before addition of Mt ligase, then the reactions were incubated at 37° C. for 1 hour.

PCR primers were produced to amplify across the region removed by restriction digest of the plasmid. The PCR reaction was carried out using Vent polymerase (NEB). Each reaction contained 100 pmol forward and reverse primers, Thermophil buffer (NEB), 2 mM dNTPs, 3 mM MgSO$_4$, 1 ul Vent Polymerase, and 5 ul of the repair reaction, and ddH$_2$O to 50 ul. The PCR cycle for SmaI/AatII was 95° C. for 5 minutes, followed by 25 cycles of 95° C. for 1 minute, 65° C. for 1 minute and 74° C. for 1 minute, with a final extension period of 10 minutes at 74° C. The cycle was the same for the HindIII/EcoRI reaction, but the annealing temperature used was 63° C., instead of 65° C.

5 ul of the PCR reaction was run on a 1% agarose Et-Br gel, and visualised under UV light. The PCR products were compared with the product given when PCR was carried out on uncut plasmid, with repaired product showing a PCR band ~400-600 bp smaller than that given by the PCR on the uncut plasmid. 5 ul of reactions showing successful repair was transformed into electro-competent XL1 blue cells, and resulting colonies were grown in 2× TY, plasmid clones purified and the repaired junctions sequenced.

Suicide Deletion Assays

The construction of the suicide deletion allele ade2::SD2 shown in FIG. 13A was as described in Karathanasis et al *Genetics* 161, 1015 (2002)). The gene conversion donor was constructed by PCR-mediated gene replacement of the CAN1 gene with a fragment of ADE2 that contains a 7-base insertion just downstream of the start codon, the same location as the I-SceI and HO sites in the suicide deletion cassettes. There was ~650 bp of ADE2 homology on each side of the cut site position. The HO suicide deletion allele shown in FIG. 13B was constructed by the same method used to create the ade2:: SD2-allele (E. Karathanasis, T. E. Wilson, *Genetics* 161, 1015 (2002)), except amplifying the GAL1-HO cassette from pGAL-HO (T. E. Wilson, M. R. Lieber, *J. Biol. Chem.* 274, 23599 (1999)) and incorporating HO cut sites. The exact sequence of all alleles is available upon request. Strains were isogenic derivatives of S288C (C. B. Brachmann et al *Yeast* 14, 115 (1998)). yku70, dn14 and rad50 mutants were made by PCR-mediated gene replacement and multiple mutants thereof were made by mating and sporulation. The data shown in FIGS. 8 to 10 were generated by growth in glucose liquid medium followed by plating to galactose plates. Data are colony counts from galactose (either Ade$^+$ or Ade$^-$) divided by colony counts from parallel glucose plates. This method reveals the absolute frequency of simple religation NHEJ (Wilson, T. E. *Genetics* 162, 677 (2002)). The data in FIGS. 11 and 12 were generated by allowing cultures to grow out in non-selective galactose liquid medium prior to plating to glucose plates. Data in graphs are the ratio of Ade$^+$ to total colonies. This method measures the frequency of imprecise NHEJ. All data points represent the average±standard deviation of at least 3 independent measurements.

Expression of Mt NHEJ Proteins in Yeast

Plasmids pNLS15 and pNLS16 are CEN plasmids (LEU2- and URA3-selectable, respectively) that direct the expression of cloned cDNAs in yeast as amino-terminal Myc epitope-NLS fusion proteins from the strong constitutive ADH1 promoter. These were made by PCR amplification of the ADH1 promoter and YKU70 terminator regions, subsequent PCR fusion via primer overhangs to generate the Myc-NLS linker region, and finally ligation into pRS415 and pRS416 (C. B. Brachmann et al *Yeast* 14, 115 (1998)). Mt Rv0937c and Rv0938 coding sequences were inserted into pNLS15 and pNLS16, respectively, by the gap repair technique. Briefly, the vectors were digested with Sma I and co-transformed into yeast with PCR fragments of the bacterial genes that contained 45 bp 5' extensions flanking the Sma I site. Following mating and sporulation to facilitate suicide deletion screening, the plasmids from a functional Ku-ligase pair were recovered from yeast and sequenced to rule out unexpected mutations. These were re-transformed into fresh yeast in parallel with vectors as needed.

Fluorescent PCR of Yeast HO Joints

~10$^8$ cells from a 2-day yeast culture in glucose synthetic defined medium lacking uracil and leucine were inoculated into fresh 25 ml of the same medium with galactose as the carbon source. This culture was shaken at 30 C for 2 days, and then diluted back 30-fold into 25 ml fresh medium lacking adenine. Following an additional 2 days shaking, ~6×10$^7$ cells were harvested and genomic DNA prepared. DNA (0.2 ug, 1.3×10$^6$ genome equivalents) was then used in a 20 µl PCR reaction with primers OW1708 (5'-HEX-CAAGTATG-GATCTCGAGGTT) (SEQ ID NO: 22) and OW1709 (5'-CTGTTCTAGAGGTACCTAGT (SEQ ID NO: 23); 25 cycles of 94 C for 15 seconds and 55 C for 15 seconds). 2 µl was then run on an 8% sequencing gel.

Yeast Joint Analysis

All colonies analyzed for the nature of their repair event were independently derived. Colonies were purified by streaking and then colony PCR was performed using primers OW603 (5'-CCTTAAGTTGAACGGAGTCC) (SEQ ID NO: 24) and OW620 (5'-CTTGACTAGCGCACTACCAG) (SEQ ID NO: 25), which amplify a 1273 bp fragment surrounding the HO or I-SceI cut sites in successful deletion events (the starting allele is too large to amplify). Recreated I-SceI sites were detected by cleavage in vitro with recombinant I-SceI (New England Biolabs) into the expected 574 and 699 bp products. All other individual joint fragments were sequenced with primer OW563 (5'-GGCAGGAGAATTTTCAGCATC) (SEQ ID NO: 26) and their microhomology mediated joining mechanism inferred by comparison with an intact I-SceI or HO cut site.

Results

Mt-Ku Binding to DNA

Recombinant histidine-tagged versions of *Mycobacterium tuberculosis* Ku-like protein [open reading frame (ORF) Rv0937c] and the genetically linked putative ATP-dependent ligase (ORF Rv0938) were found to be readily over expressed in soluble form in *E. coli*. These proteins (designated Mt-Ku and Mt-Lig) were purified by nickel-agarose affinity chromatography.

Analysis of recombinant Mt-Ku by gel-filtration chromatography indicated that Mt-Ku exists as a homodimer in solution. This species was very stable, even at high salt concentrations, which provides indication of a strong homodimeric interaction. Electrophoretic mobility-shift assays (EMSAs), with a 33-base-pair (bp) dsDNA oligonucleotide with either 5' or 3' overhangs, demonstrated that Mt-Ku, like eukaryotic Ku, forms a specific complex with either type of DNA end. Excess non-labelled linear dsDNA, but not closed circular plasmid DNA or single-stranded DNA, competed for binding, which demonstrates that Mt-Ku binds preferentially to dsDNA ends.

Titration of Mt-Ku against fixed concentration of labelled 33-nucleotide oligomer resulted in a single retarded band, presumably representing a 1:1 Ku-DNA complex. When the length of the DNA was doubled (66-nucleotide oligomer), two progressively retarded bands were observed. Multiple Ku-DNA complexes were formed on all dsDNA linear substrates of >60-mer tested, and the number of retarded species was directly proportional to the length of the DNA, indicating that, after binding to the end, Mt-Ku can freely move along the DNA.

Mt-Lig Substrate

To test whether Mt-Lig uses ATP or NAD+, Mt-Lig was incubated with either [α-32P] ATP or NAD+ and magnesium. In the presence of ATP, but not NAD+, a radiolabelled covalent ligase-adenylate adduct was formed that co-migrated with the Mt-Lig polypeptide during SDS-polyacrylamide gel electrophoresis (SDS-PAGE). This demonstrates that Mt-Lig is active in covalent nucleotidyl transfer with a specific preference for ATP as the AMP donor.

Substitution of the motif I residue Lys481 by alanine (K481A) abolished ligase-AMP formation.

Ligase Activity of Mt-Lig

To examine whether Mt-Lig is a dsDNA ligase, dsDNA substrates of various sizes (53 to 2560 bp) were used in ligation reactions and the efficiency of ligation compared to that mediated by T4 DNA ligase. Mt-Lig catalyzed the joining of the various dsDNA fragments of different lengths to equivalent extents. *M. tuberculosis* Mt-Lig is therefore a functional DNA ligase capable of catalyzing DSB rejoining in an ATP-dependent manner.

Notably, the DNA ligation activity of Mt-Lig was stimulated >30-fold by the addition of Mt-Ku. Stimulation was abolished by heat denaturation of Mt-Ku. Mt-Lig was not stimulated by the human Ku heterodimer and, conversely, human ligase IV/XRCC4 and T4 ligase were not stimulated by Mt-Ku. Indeed, amounts of Mt-Ku that stimulated Mt-Lig inhibited both ligase IV and T4 ligase activity. Consistent with these observations, Mt-Ku stimulated the activity of Mt-Lig by 20-fold but not T4 ligase in an in vitro plasmid repair assay. Stimulation of ligation by Mt-Ku is therefore highly specific for Mt-Lig and provides indication that these proteins physically interact.

Potential interactions between Mt-Ku and Mt-Lig were investigated by EMSAs with a radiolabelled dsDNA probe (33 bp). Including Mt-Lig and Ku together led to the generation of a DNA/protein complex with a mobility distinct from that of the complexes formed by either protein alone. However, the addition of increasing amounts of Mt-Ku did not abolish the appearance of the novel DNA-protein complex, which demonstrates that Mt-Ku does not inhibit the binding of Mt-Lig to DNA. Formation of the new complex did not occur when Mt-Lig had been heat denatured, which indicates that the complex reflects the binding of Mt-Lig and is not mediated by a buffer component. Biacore studies with a biotinylated dsDNA (33-mer) bound to a streptavidin coated chip and isothermal titration calorimetry studies also confirmed that Mt-Ku specifically recruits Mt-Lig to DNA.

To determine whether Mt-Lig has RNA primase activity, recombinant Mt-Lig was incubated with a poly dT homopolymer and [α-32P] ATP. Mt-Lig was observed to synthesize oligoribonucleotides ranging in length from 1-50 nucleotides. In a similar assay with a single strand DNA template, Mt-Lig also synthesized RNA primers.

Mt-lig was assayed for DNA-dependent DNA primase activity using complementary single stranded oligonucleotides. Annealing of the complementary single-strands resulted in a 5-nt overhang in the bottom strand. Mt-Lig filled the overhangs with either dNTPs or rNTPs confirming the presence of both DNA-dependent DNA and RNA polymerase activities. Replacement of two invariant Asp residues in motif I of Mt-Lig with alanine residues abolished the polymerase activity of Mt-Lig.

Polymerisation assays were performed with DNA duplex oligonucleotides that generate a non-ligatable one nucleotide (nt) gap and a 5-base 3' overhang upon alignment (FIG. 4A). Mt-Lig efficiently filled in the gap with no detectable strand displacement synthesis (FIG. 5A, left panel). Addition of a phosphate group to the 5' terminus of the 1-nt gap, resulted in gap-filling and ligation (FIG. 5A, right panel), indicating the concerted action of Mt-Lig polymerase and ligase activities on NHEJ intermediates.

Mt-Lig progressively digested the 3' single-strands (ss) but not the 5' ss tails of partial duplexes until reaching the double-strand (ds) region (FIG. 5B). Thus, Mt-Lig possesses 3' to 5' ss DNA exonuclease activity. Using DNA substrates that generate a 3'-flap adjacent to a nick, Mt-Lig removed the flap by exonucleolytic digestion, generating a base-paired linear duplex (FIG. 5C). At higher concentrations the nuclease progressed through the microhomology region and into the duplex (FIG. 5C). Similar results were obtained when there was a gap adjacent to the mismatched flap. Nuclease activity was dependent on the presence of a divalent cation such as magnesium or manganese. Replacement of a conserved histidine residue (H373) with alanine abolished this exonuclease activity, confirming that the nuclease activity is also an intrinsic property of Mt-Lig.

The Mt-Lig complex was examined to see if it could repair a double strand break (DSB) junction containing non-compatible ends requiring full end processing prior to ligation.

In the presence of NTPs, Mt-Lig joined aligned DNA duplexes possessing a 1-nt 3' flap adjacent to 3-nt gap (FIG. 6A). A similar, albeit less efficient reaction, was observed in the presence of dNTPs. Neither the nuclease or polymerase mutant proteins were able to repair this junction, confirming that both activities are required to process the DSB prior to ligation. A synthetic DNA DSB junction was designed that contained a micro-homology (4 bp), a ssDNA gap (5 bp) and a 3' ssDNA flap structure (3 bp).

Sequencing of ligated junctions generated by Mt-Lig in assays with this substrate with a 3-nt flap adjacent to a 5-nt gap revealed that microhomology sequence was retained and the mismatched flap was replaced by nucleotides complementary to the template strand.

Mt-Lig was observed to be capable of removing the 3' flap overhang. However, the 3' processing activity also excised the micro-homology sequence back to the ds DNA junction. Similar processing activity was also observed on gapped, micro-homology substrates with no 3' flap. These findings confirm that Mt-Lig possesses a structure specific 3' exonuclease that removes 3' overhangs of DNA ends or DSBs.

Mt-Lig was assayed for both DNA and RNA "filling-in" activity on the micro-homology DSB substrate. Mt-Lig synthesized DNA or RNA, depending on the nucleotide added, and effectively filled in the 5 bp gap.

The effect of Mt-Lig on DNA molecules with incompatible ends was assessed. In the presence of nucleotides (NTPs or dNTPs), ATP and magnesium, the three catalytic activities of Mt-Lig were observed to act in a concerted manner to selectively and precisely process DNA molecules with incompatible ends and join the resulting reconstituted compatible ends.

In the first step of Mt-Lig mediated ligation, the 3' nuclease activity cleaves away 7 bp (3 bp flap plus 4 bp micro-homology) leaving a dsDNA end. The nucleolysis step is followed by a polymerisation step to fill in the resulting gap, visible as a ladder of incompletely filled-in products. Finally, the fully extended strand is ligated to the 5' phosphate of the other DSB yielding one of the most abundant species, the fully ligated DSB. Sequencing of the repaired DSB junctions confirmed that the flap was removed and replaced with the sequence of the complementary template strand.

Mt-Ku specifically stimulated joining of fully complementary ss-ends by Mt-Lig as described above. The impact of Mt-Ku on the other activities of Mt-Lig was examined. Mt-Ku had no significant effect on the removal of mismatched flaps, but did inhibit further digestion into the microhomology region (FIG. 6B), providing indication that Mt-Ku remains physically associated with this region during repair.

The role of Mt-Ku was examined using an in vitro PCR-based plasmid repair assay (D. A. Ramsden et al *Nature* 388 488 (1997)) In this assay, plasmid DNA was cut with different pairs of restriction enzymes, incubated with Mt-Lig in the presence or absence of Mt-Ku, and finally the repaired DSB junction was amplified by PCR and sequenced. Mt-Ku was observed to dramatically stimulate joining of long linear DNA molecules with different incompatible ends by Mt-Lig (FIG. 6C). Processing and joining occurred in the presence of either dNTPs or NTPs (FIG. 6C). In contrast, no rejoining was observed by T4 ligase in the presence or absence of Mt-Ku (FIG. 6C). Joining of partially complementary 5' (HindIII-NheI) and 3' (PstI-KpnI) overhangs appeared to require microhomology-mediated alignments that need gap filling and, in some instances, 3' flap removal on one strand (Table 1). Joining of blunt end-3' single-strand overhang (SmaI-AatII) appeared to require the addition of one nucleotide by the terminal transferase activity, followed by microhomology pairing with the 3' overhang, flap resection, gap filling, and ligation (Table 1). In all cases, gap-filling accurately copied the template strand.

These findings demonstrated that Mt Ku and ligase can perform NHEJ in vitro. To establish if the complex could mediate-rejoining of chromosomal breaks in viva, a variant of the yeast-based "suicide deletion" assay was employed (E. Karathanasis et al Genetics 161, 1015 (2002); Wilson, T. E., Genetics 162, 677 (2002)). This allowed the simultaneous determination of NHEJ and recombination frequencies.

~75% of wild-type yeast cells repaired the I-SceI DSB by recombination and ~2% by NHEJ, with the remainder dying (FIG. 8). NHEJ occurred predominantly by simple religation (Ade+ colonies) and was ~100-fold decreased by yku70 (Ku) deletion. Introducing plasmids expressing Mt-Ku and Mt-Lig restored NHEJ to ~50% of the wild-type yeast level (FIG. 8). The pattern seen with combinations of Mt-Ku, Mt-Lig and yku70 and dn14 (ligase) mutations demonstrated that Mt NHEJ was truly reconstituted by a concerted species-specific interaction of the Ku and ligase proteins independent of yeast NHEJ (FIG. 9).

In the yeast S. cerevisiae, NHEJ is also dependent upon the Mre11/Rad50/Xrs2 complex (MRX). MRX may act as an end-bridging factor and/or functionally interact with yeast Ku and Dn14/Lif1. Expression of the Mt NHEJ proteins in yeast rad50 mutants substantially recovered NHEJ (FIG. 10), although to a lesser extent than seen with yku70 or dn14 mutants. Thus, Mt NHEJ reconstitution in yeast required neither MRX nor its bacterial orthologue SbcCD, demonstrating that MRX-family function is not obligatorily required for tethering of chromosome ends during NHEJ.

As with NHEJ mediated by yeast proteins (T. E. Wilson et al Nature 388, 495-498 (1997)), Mt NHEJ reconstituted in yeast occasionally resulted in imperfect repair, evident as Ade⁻ colonies in the absence of the gene conversion donor. Sequencing 15 of these colonies revealed a variety of junctions that occurred predominantly by mispairing of the A/T-rich I-SceI 3' overhangs.

To create a suicide deletion system that selects specifically for NHEJ events involving such end processing, HO was substituted for I-SceI so that +2 (or −1, −4, etc.) frame-shifted joints yield Ade+ colonies. ~0.75% of all NHEJ events in wild-type yeast were Ade+ (FIG. 11), and >50% of these were HO(+2) joints (FIG. 11). With Mt NHEJ reconstituted, the overall frequency of NHEJ remained high, but the percentage of Ade+ events was substantially decreased (FIG. 11). Although some HO(+2) processed joints were formed, the HO(−1) joint now predominated (FIG. 12), providing a signature for Mt NHEJ. Strikingly, Mt NHEJ proteins shifted the HO joint pattern and Ade+ frequency to match that observed for Mt NHEJ even in wild-type yeast (FIG. 11). Mt-Ku and Mt-Lig proteins can therefore catalyze processed NHEJ in chromosomes, but, despite this ability, repair is highly accurate at compatible DSB ends.

The above findings demonstrate that Mt-Lig possesses the nuclease, ligase and polymerase activities which are required for non-homologous end joining (NHEJ). NHEJ repair assays further show that the activities of this polypeptide act in a concerted manner to selectively and precisely process DNA molecules with incompatible ends and join the resulting reconstituted compatible ends, allowing the NHEJ pathway to be reconstituted in vitro and in vivo using Mt-Lig.

TABLE 1

| Non-homologus ends | No. of clones | Predicted intermediates | Repaired NHEJ junction |
|---|---|---|---|
| HindIII   NheI<br>----A     CTAGC----<br>----TTCGA      G---- | 10 | ----A   CTAGC----<br>----TTCGA   G----<br>microhomology,<br>filling-in & ligation | ----AAGCTAGC----<br>----TTCGATCG---- |
|  | 1 | ----A   CTAGC----<br>----TTCGA   G----<br>Mispairing, followed by<br>filling-in, replacing of incorrect<br>base & ligation | ----AAGCTTAGC----<br>----TTCGAATCG---- |
| AatiI  SmaI<br>----GACGT  GGG----<br>----C       CCC---- | 10 | ----GACG    GGG----<br>----C      CCCC---- | ----GACGGGG----<br>----CTGCCCC---- |
|  | 2 | ----GAC    GGG----<br>----C      GCCC----<br>Removal of nucleotide(s),<br>addition of a single nucleotide<br>to 3' end, base pairing,<br>tilling-in & ligation | ----GACGGG----<br>----CTGCCC---- |
| PstI  KpnI<br>----CTGCA    C----<br>----G    CATGG---- | 6 | ----CTGCA C----<br>----G CATGG---- | ----CTGTACC----<br>----GACATGG---- |
|  | 8 | ----CTGCA C----<br>----G CATGG----<br>base pairing, removal of<br>extra nucleotides,<br>filling-in, & ligation | ----CTGCACC----<br>----GACGTGG---- |

TABLE 2

| Motif | | I | | III | | IIIa | | IV | | V | | VI | |
|---|---|---|---|---|---|---|---|---|---|---|---|---|---|
| Bs ykoU: | 21- | EVKYDGVR (SEQ ID NO: 27) | -43- | LTLDGEIV (SEQ ID NO: 28) | -34- | CFIAPDLLERSG (SEQ ID NO: 29) | -57- | EGIVA (SEQ ID NO: 30) | -15- | WLKYKNFKQAY (SEQ ID NO: 31) | -82- | IGFEFQMDWTE (SEQ ID NO: 32) | -304 |
| Bh 2209: | 20- | EVKYDGFR (SEQ ID NO: 33) | -43- | ITIDGELV (SEQ ID NO: 34) | -34- | TLLAFDILELKG (SEQ ID NO: 35) | -57- | EGVVA (SEQ ID NO: 36) | -15- | WLKKKNFRQVT (SEQ ID NO: 37) | -81- | HRFRLDVKPAQ (SEQ ID NO: 38) | -306 |
| Mt Lig C: | 26- | EPKWDGFR (SEQ ID NO: 39) | -38- | CVIDGEII (SEQ ID NO: 40) | -32- | SFIAFDLLALGD (SEQ ID NO: 41) | -54- | DGVIA (SEQ ID NO: 42) | -13- | MFKIKHLRTAD (SEQ ID NO: 43) | -114- | TAQFNRWRPDR (SEQ ID NO: 43) | -26 |
| Bs yoqV: | 22- | ELKFDGIR (SEQ ID NO: 45) | -35- | TVLDGEVI (SEQ ID NO: 46) | -26- | VYCVFDVIYKDG (SEQ ID NO: 47) | -47- | EGIVI (SEQ ID NO: 48) | -15- | WLKVINYDYTE (SEQ ID NO: 49) | -81- | | |
| Pa 2138: | 235- | ELKLDGYR (SEQ ID NO: 50) | -38- | SWLDGELV (SEQ ID NO: 51) | -35- | LYVLFDLPYHEG (SEQ ID NO: 52) | -49- | EGVIG (SEQ ID NO: 53) | -14- | WIKLKCQLRQE (SEQ ID NO: 54) | -111- | AREVTGERPAG (SEQ ID NO: 55) | -313 |
| Mt Rv-0938: | 478- | EGKWDGYR (SEQ ID NO: 56) | -38- | VVLDGEAV (SEQ ID NO: 57) | -22- | EFWAFDLLYLDG (SEQ ID NO: 58) | -46- | EGVIA (SEQ ID NO: 59) | -15- | WVKDKHWNTQE (SEQ ID NO: 60) | -98- | SSWRGLRPDK (SEQ ID NO: 61) | -8 |
| Bact ATP Consensus: | | s.KhDGhR (SEQ ID NO: 62) | | ..hpGEhh (SEQ ID NO: 63) | | .h.hFDh....s (SEQ ID NO: 64) | | Eghhh (SEQ ID NO: 65) | | hhK.K...... | | ............ | |
| T7 Lig: | 31- | ELKYDGVR (SEQ ID NO: 66) | -48- | FMLDGELM (SEQ ID NO: 67) | -49- | HIKLYAILPL-- (SEQ ID NO: 68) | -62- | EGLIV (SEQ ID NO: 69) | -14- | WWKMKPENEAD (SEQ ID NO: 70) | -96- | PSFVM-FRGTE (SEQ ID NO: 71) | -7 |

The invention claimed is:

1. A method of modifying a nucleic acid molecule comprising:
contacting the nucleic acid molecule with an isolated prokaryotic DNA ligase polypeptide in the presence of a prokaryotic Ku polypeptide, wherein the prokaryotic DNA ligase polypeptide has at least 95% amino acid sequence identity with the amino acid sequence of SEQ ID NO: 91 and the prokaryotic Ku polypeptide has at least 95% amino acid sequence identity with the amino acid sequence of SEQ ID NO: 92.

2. A method of ligating nucleic acid molecule ends comprising:
contacting a first nucleic acid end and a second nucleic acid end with an isolated prokaryotic DNA ligase polypeptide in the presence of a prokaryotic Ku polypeptide,
wherein said first and said second nucleic acid ends comprise non-complementary overhang regions, and
wherein the prokaryotic DNA ligase polypeptide has at least 95% amino acid sequence identity with the amino acid sequence of SEQ ID NO: 91 and the prokaryotic Ku polypeptide has at least 95% amino acid sequence identity with the amino acid sequence of SEQ ID NO: 92.

3. The method according to claim 2 wherein the first end is on a first nucleic acid molecule and the second end is on a second nucleic acid molecule.

4. The method according to claim 3 wherein the first and second nucleic acid molecules are DNA.

5. The method according to claim 3 wherein the first nucleic acid molecule is DNA and the second nucleic acid molecule is RNA.

6. The method according to claim 2 wherein the first and second ends are on the same nucleic acid molecule.

7. The method according to claim 2 further comprising isolating the ligated nucleic acid molecule, purifying the ligated nucleic acid molecule, or both isolating and purifying the ligated nucleic acid molecule.

8. A method of filling in a single stranded gap in a double stranded nucleic acid molecule comprising:
contacting a double stranded nucleic acid molecule having a single stranded region with an isolated prokaryotic DNA ligase polypeptide in the presence of a prokaryotic Ku polypeptide, wherein the prokaryotic DNA ligase polypeptide has at least 95% amino acid sequence identity with the amino acid sequence of SEQ ID NO: 91 and the prokaryotic Ku polypeptide has at least 95% amino acid sequence identity with the amino acid sequence of SEQ ID NO: 92.

9. The method according to claim 8 wherein said nucleic acid molecule and said prokaryotic DNA repair ligase polypeptide are contacted in the presence of NTPs.

10. The method according to claim 8 wherein said nucleic acid molecule and said prokaryotic DNA repair ligase polypeptide are contacted in the presence of dNTPs.

11. A method of removing a single stranded overhang from the end of a nucleic acid molecule comprising:
contacting said nucleic acid molecule with an isolated prokaryotic DNA ligase polypeptide in the presence of a prokaryotic Ku polypeptide, wherein the prokaryotic DNA ligase polypeptide has at least 95% sequence identity with the amino acid sequence of SEQ ID NO: 91 and the prokaryotic Ku polypeptide has at least 95% amino acid sequence identity with the amino acid sequence of SEQ ID NO: 92.

12. The method according to claim 11 wherein said nucleic acid molecule is contacted in the presence of $Mg^{2+}$ or $Mn^{2+}$.

* * * * *